(12) United States Patent
Chilkoti

(10) Patent No.: US 6,582,926 B1
(45) Date of Patent: Jun. 24, 2003

(54) METHODS OF USING BIOELASTOMERS

(75) Inventor: Ashutosh Chilkoti, Durham, NC (US)

(73) Assignee: Duke University, Durham, NC (US)

( * ) Notice: Subject to any disclaimer, the term of this patent is extended or adjusted under 35 U.S.C. 154(b) by 106 days.

(21) Appl. No.: 09/695,483

(22) Filed: Oct. 24, 2000

Related U.S. Application Data

(63) Continuation-in-part of application No. 09/273,025, filed on Mar. 19, 1999.

(51) Int. Cl.[7] .............................................. G01N 33/53

(52) U.S. Cl. .................. 435/7.1; 435/287.1; 435/287.8; 435/287.9; 436/518; 436/532; 436/533; 436/539

(58) Field of Search ............................... 435/7.1, 287.1, 435/287.8, 287.9; 436/518, 532, 533, 539

(56) References Cited

U.S. PATENT DOCUMENTS

| | | | |
|---|---|---|---|
| 4,474,851 A | 10/1984 | Urry | 428/373 |
| 4,749,647 A | 6/1988 | Thomas et al. | 435/6 |
| 4,752,638 A | 6/1988 | Nowinski et al. | 525/54.1 |
| 5,288,514 A | * 2/1994 | Ellman | |
| 5,445,934 A | * 8/1995 | Fodor et al. | |
| 5,624,711 A | * 4/1997 | Sundberg et al. | |

(List continued on next page.)

OTHER PUBLICATIONS

Monji, et al., *A novel immunoassay system and bioseparation process based on thermal phase separating polymers*, Applied Biochemistry & Biotechnology, vol. 14, pp. 107–120 (1987).

Wu, Xue Shen, et al., *Conjugation of phosphatidylethanolamine to poly(N–isopropylacrylamide) for potential use in liposomal drug delivery systems*, Polymer, vol. 33, No. 21, pp. 4659–4662 (1992).

Nguyen, A.L., et al., *Syntheses and Applications of Water–Soluble Reactive Polymers for Purification and Immobilzation of Biomolecules*, Biotechnology and Bioengineering, vol. 34, pp. 1186–1190 (Nov. 1989).

Umeno, Daisuke, et al., *Temperature–Induced Precipitation of Specific DNA Fragments Using DNA–POLY(N–isopropylacrylamide) Conjugate*, Chemistry Letters, pp. 381–382 (1999).

Umeno, Daisuke, et al., *Single stranded DNA–poly(N–isopropylacrylamide) conjugate for affinity precipitation separation of oligonucleotides*, Chem. Commun., pp. 1433–1434 (1998).

Takei, Yoshiyuki, et al., *Temperature–Responsive Bioconjugates. 3. Antibody–Poly(N–isopropylacrylamide) Conjugates for Temperature–Modulated Precipitations and Affinity Bioseparations*, Bioconjugate Chem., vol. 5, pp. 577–582 (1994).

Takei, Yoshiyuki, et al., *Temperature–Responsive Bioconjugates. 1. Synthesis of Temperature–Responsive Oligomers with Reactive End Groups and Their Coupling to Biomolecules*, Bioconjugate Chem, vol. 4, pp. 42–46 (1993).

Takei, Yoshiyuki, et al., *Temperature–Responsive Bioconjugates. 2. Molecular Design for Temperature–Modulated Bioseparations*, Bioconjugate Chem., vol. 4, pp. 341–346 (1993).

Stayton, patric S., et al., *Control of protein–ligand recognition using a stimuli–responsive polymer*, Nature, vol. 378, pp. 472, 474 (Nov. 30, 1995).

Monjui, Nobuo, et al, *A Novel Immunoassay System and Bioseparation Process Based on Thermal Phase Separating Polymers*, Applied Biochemistry and Biotechnology, vol. 14, pp. 107–120 (1987).

Monji, Nobuo, et al., *Application of a Thermally–Reversible Polymer–Antibody Conjugate in a Novel Membrane–Based Immunoassay*, Biochemical and Biophysical Research Communications, vol. 172, No. 2, pp. 652–660 (Oct. 30, 1990).

Maeda, Mizuo, et al., *Modification of DNA with poly(N–isopropylacrylamide) for thermally induced affinity separation*, Reactive Polymers, vol. 21, pp. 27–35 (1993).

Chen, Guohua, et al., *A new temperature–and pH–responsive copolymer for possible use protein conjugation*, Macromol. Chem. Phys., vol. 196, pp. 1251–1259 (1995).

Galaev, I. Yu, et al., *Affinity Thermoprecipitation: Contribution of the Efficiency of Ligand–Protein Interaction and Access of the Ligand*, Biotechnology and Bioengineering, vol. 41, pp. 1101–1106 (1993).

Chen, Guohua, et al., *Preparation and Properties of Thermoreversible, Phase–Separating Enzyme–Oligo(N–isopropylacrylamide) Conjugates*, Bioconjugate Chem., vol. 4, pp. 509–514 (1993).

Chen, Jing Ping, et al., *Polymer–protein conjugates; II. Affinity precipitation separation of human immunogammaglobulin by a poly(N–isopropylacrylamide)–protein A conjugate*, Biomaterials, vol. 11, pp. 631–634 (Nov., 1990).

International Search Report dated Aug. 15, 2000; International Application No. PCT/US00/05780.

Abstract, Woods, et al., *Protein Nanopatterning on a Gold/Aluminum Nanoarray*, Vacuum, Thin Films, Surface/Interfaces and Processes, 46th International Symposium, p. 156 (Oct. 25–29, 1999).

*Primary Examiner*—Bao-Thuy L. Nguyen
(74) *Attorney, Agent, or Firm*—Myers Bigel Sibley & Sajovec

(57) ABSTRACT

Bioelastomers are disclosed for use in methods of binding compounds including immunoassay methods, in biosensors and methods or regenerating biosensors, and in methods for targeting the delivery of a compound to a particular location within an animal subjects. In general, the bioelastomer is conjugated to a binding compound, which is in turn used to bind a compound of interest. For targeted compound delivery, the bioelastomer is conjugated to the compound to be delivered.

27 Claims, 12 Drawing Sheets

U.S. PATENT DOCUMENTS

| | | | |
|---|---|---|---|
| 5,702,717 A | 12/1997 | Cha et al. | 424/425 |
| 5,816,259 A | 10/1998 | Rose | 128/898 |
| 5,900,405 A | 5/1999 | Urry | 514/17 |
| 5,998,588 A | 12/1999 | Hoffman et al. | 530/402 |
| 6,004,782 A | 12/1999 | Daniell et al. | 435/71.2 |
| 6,329,209 B1 * | 12/2001 | Wagner et al. | |

* cited by examiner

1 Chip incubation with 1 μM ELP-18-TRX externally
2 Flush reference channel with water
3 Exchange running buffer to 1 M NaCL
4 Incubate channel 1 with A-TRX Fab
5 Change temperature from 35 °C to 20 °C

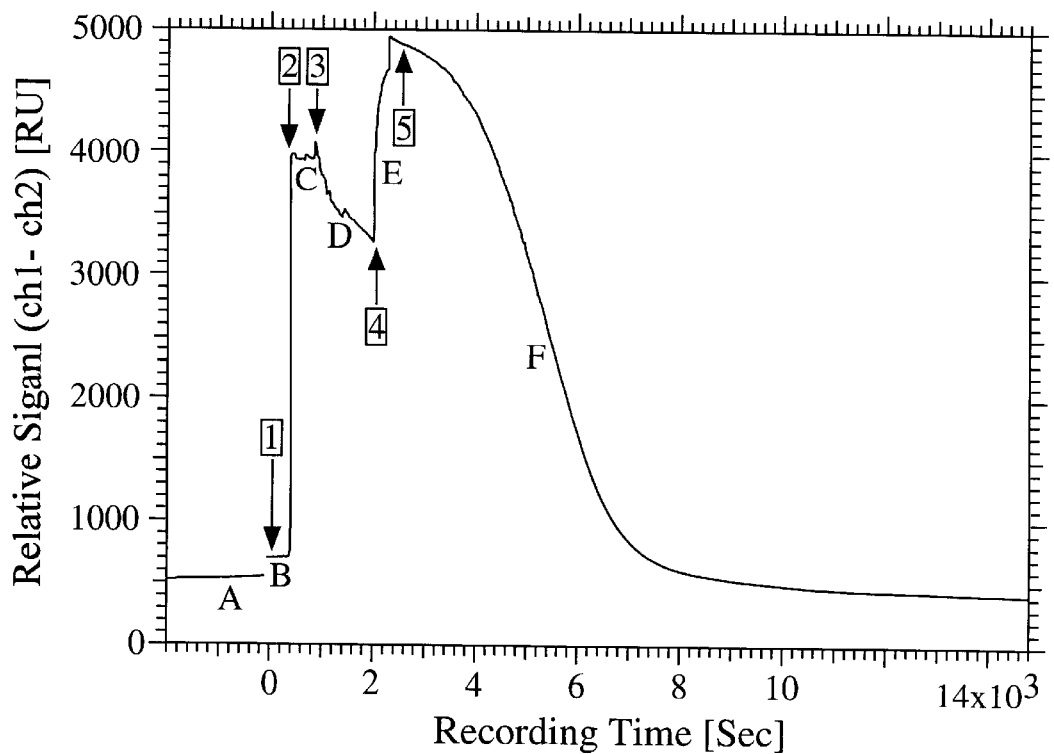

A  Pure gold chip with C16-thiol
B  Absorbed ELP-18-TRX on both channels
C  ELP-18-TRX (Ch. 1), Au-C16-thiol (Ch. 2)
D  ELP partially desorbs due to lower salt conc.
E  Binding of A-TRX Antibody
F  Desorption of ELP-18-TRX/A-TRX complex

FIG. 6

SEQUENCE LISTING

<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: X = any amino acid

<400> SEQUENCE: 1

Val Pro Gly Xaa Gly
1               5

METHODS OF USING BIOELASTOMERS

RELATED APPLICATIONS

This application is a continuation-in-part of commonly owned, copending application Ser. No. 09/273,025, filed Mar. 19, 1999, the disclosure of which is incorporated by reference herein in its entirety.

STATEMENT OF FEDERAL SUPPORT

This invention was made with United States Government support under Grant Number GM57373 awarded by the National Institute of Health. The United States Government has certain rights in this invention.

FIELD OF THE INVENTION

The present invention concerns bioelastic polymers and methods of use thereof, particularly for immunoassays, for the production of regenerable biosensors, for the localized delivery of compounds in vivo, and for the patterning of molecules on substrates.

BACKGROUND OF THE INVENTION

Numerous bioelastic polymers, also known as bioelastomers or elastin-like proteins ("ELPs") are known. Examples are described in D. Urry et al., A Simple Method for the Purification of a Bioelastic Polymer, PCT Application WO 96/32406. Such compounds are proteins or peptides, typically polypeptides, that exhibit an inverse temperature transition: that is, the compounds condense at a higher temperature range in an aqueous system on raising the temperature of the compounds through their transition temperature ($T_t$). Bioelastic polymers are soluble in water at a sufficiently low temperature, but hydrophobically fold and associate to form a separate phase as the temperature is raised through a particular temperature range.

1. Separation and Immunoassay Systems

Immunoassays are commonly used to detect analytes such as enzymes, hormones, drugs, and other molecules of interest in complex biological mixtures. By definition, an immunoassay relies on the specific binding of an antigen by an antibody, but assays using other biological high affinity binding partners (e.g., ligand-cell surface receptor, inhibitor-enzyme, etc.) can also be employed in an analogous manner. A number of different immunoassay formats have been developed to detect and/or quantitate the levels of analytes; for a review of immunoassays, see PCT Patent Application WO 86/06492.

2. Biosensor Systems and Biosensor Regeneration

Ligand-binding proteins such as receptors and antibodies, currently used in biosensors, can detect specific analytes (ligands) with high sensitivity in the presence of potential interference's in complex mixtures. The high affinity of protein-analyte interactions is the basis of their exquisite sensitivity. However, high affinity is generally accompanied by an extremely slow dissociation rate (off rate) of the protein-ligand complex. Therefore, in practice, most biosensors are "one shot" devices; dosimeters rather than continuous sensors or alternatively, sensors with very slow response times. In order to use biosensors for the semi-continuous, in situ monitoring of analytes, or for subsequent rounds of sensing in batch mode, the sensor must be regenerated for reuse in an expedient time frame.

There are two possible approaches to sensor regeneration. When the receptor is covalently coupled to the sensor surface, free receptor can be regenerated by displacing the bound analyte. Unfortunately, methods to gently and reversibly regenerate analyte-free receptor do not currently exist: most current methods disrupt noncovalent interactions between analyte and receptor by partially denaturing the receptor using drastic changes in the protein-ligand environment such as low pH (<3), or high chaotrope concentration, conditions which often irreversibly denature the protein after a few rounds of regeneration.

If the receptor is not covalently attached to the substrate, a second method for surface regeneration is feasible where the surface itself can be regenerated by removing the analyte-bound receptor from the surface. The potential advantage is that the analyte "sees" fresh receptor in every round of sensing, which can decrease drift in the sensor response and maintain high affinity and homogenous binding kinetics. This approach to sensor regeneration is difficult to broadly implement because noncovalent methods to immobilize proteins on surfaces typically involves their physical adsorption, which is typically irreversible, and subsequent stripping of adsorbed protein with detergents or chaotropes is frequently incomplete. In order to noncovalently and reversibly bind a receptor to the surface, methods must be found to reversibly control the physicochemical properties of the receptor such that the adsorption-desorption process can be triggered reversibly.

3. Targeted Delivery of Therapeutics to Solid Tumors by Thermally-Responsive Polymers The targeted delivery of drugs to solid tumors is a complex problem because of the impediments to drug delivery that are posed by tumor heterogeneity. Cancer cells typically occupy less than half of the total tumor volume. Approximately 1–10% is contributed by tumor vasculature, and the rest is occupied by a collagen-rich interstitium. The major impediments to drug delivery arise from heterogeneous distribution of blood vessels, combined with aberrant branching and tortuosity, which results in uneven and slowed blood flow. The leakiness of tumor vessels combined with the absence of a functional lymphatic system results in an elevated interstitial pressure, which retards the convective transport of high MW (>2000 Da) drugs. R. Jain, Sci. Am. 271: 58–65 (1994). The heterogeneity of antigen and receptor expression in tumors is an additional problem in affinity-targeted delivery of drugs to solid tumors.

Front-line therapies for different tumors include surgery, chemotherapy, and radiation. The infiltrative nature of many solid tumors often prevents complete surgical resection because of the high risk of compromising function, thereby necessitating postoperative chemotherapy and/or radiotherapy. However, chemotherapy, particularly when delivered systemically is of limited effectiveness due to inadequate drug delivery, systemic toxicity, and a markedly variable biological sensitivity. External beam irradiation, while useful for many types of tumors, is also limited by dose limiting toxicity to healthy tissue.

Two other treatment modalities that have been suggested for the treatment of solid tumors, are hyperthermia [S. Field and J. Hand, An Introduction to the Practical Aspects of Clinical Hyperthermia (Taylor and Francis, London 1990)] and targeted radiotherapy [C. Hoefnagel., Int. J. Biol. Markers 8: 172 (1993); M. Gaze, Phys. Med. Biol. 41: 1895 (1993)]. The use of local hyperthermia as a therapeutic modality for sold tumors is motivated by the increased thermal sensitivity of tumor vasculature compared to normal vasculature. Hyperthermia, at temperatures between 40 and 42° C., is known to increase tumor blood flow and vascular permeability. Because hyperthermia sensitizes cells to radiation, it has been combined with radiation therapy to increase tumor cytotoxicity [M. Hauck et al., in Handbook of Targeted Delivery of Imaging Agents, pp. 335–361 (V. Torchilin Ed. 1995)].

The limitations of current therapeutic approaches for the management of solid tumors provide a compelling need for the development of improved modalities for the targeted delivery of therapeutics.

SUMMARY OF THE INVENTION

A first aspect of the present invention is a method of binding a compound of interest in an aqueous solution. The method comprises the steps of:

(a) providing a conjugate comprising a bioelastic compound and a binding compound, wherein the binding compound specifically binds the compound of interest, and wherein the bioelastic compound has a transition temperature below which the bioelastic compound is soluble in the solution, and above which the bioelastic compound is insoluble in the solution;

(b) contacting the conjugate to the compound of interest in an aqueous solution so that the compound binds thereto, with the contacting step carried out at a temperature below the transition temperature of the bioelastic compound; and then (c) raising the temperature of the conjugate to a temperature above the transition temperature of the bioelastic compound so that the conjugate separates from the aqueous solution with the compound of interest bound thereto. Separation may be passive (e.g., precipitation in solution) or active (e.g., by centrifugation or filtration). Thus, the step of "raising the temperature" may be thought of as being followed by a step of separating (i.e., actively separating) the conjugate with the compound of interest bound thereto from the solution.

A second aspect of the present invention is a method useful for immunologically detecting an analyte in an aqueous solution. The method comprises the steps of:

(a) providing a conjugate comprising a bioelastic compound and a binding compound, wherein the binding compound specifically binds the analyte, and wherein the bioelastic compound has a transition temperature below which the bioelastic compound is soluble in the solution, and above which the bioelastic compound is insoluble in the solution;

(b) contacting the conjugate to the analyte in an aqueous solution so that the compound binds thereto, with the contacting step carried out at a temperature below the transition temperature of the bioelastic compound;

(c) raising the temperature of the conjugate to a temperature above the transition temperature of the bioelastic compound so that the conjugate separates from the aqueous solution with the analyte bound thereto; and then (d) detecting the analyte.

A third aspect of the present invention is an article useful as a regenerable biosensor for binding a compound of interest from an aqueous solution, or for any such other purposes to which the article may be suitable. The article comprises:

(a) a solid support having a hydrophobic surface formed thereon; and (b) a conjugate reversibly bonded to the hydrophobic surface, the conjugate comprising (i) a bioelastic compound and a (ii) binding compound, wherein the binding compound specifically binds the compound of interest, and wherein the bioelastic compound has a transition temperature below which the bioelastic compound is soluble in the solution, and above which the bioelastic compound is insoluble in the solution; so that the biosensor may be used to bind the compound of interest at a temperature above the transition temperature, and so that the conjugate can be removed from the solid support for recycling of the article by lowering the temperature of the solid support (and/or the solution; so long as the temperature of the conjugate is lowered) below the transition temperature.

A fourth aspect of the invention is a method of recycling a used biosensor to which has been bound a compound of interest. The method comprises:

(a) providing a biosensor comprising a solid support having a hydrophobic surface formed thereon and a first conjugate reversibly bonded to the hydrophobic surface, the conjugate comprising (i) a bioelastic compound (which is bonded to the hydrophobic surface by hydrophobic interactions when at a temperature above its transition temperature) and (ii) a binding compound, wherein the binding compound has the compound of interest specifically bound thereto, and wherein the bioelastic compound has a transition temperature below which the bioelastic compound is soluble in the solution, and above which the bioelastic compound is insoluble in the solution; and then (b) separating the conjugate with the compound of interest bound thereto from the solid support by lowering the temperature of the biosensor to below the transition temperature; and then (c) binding a second conjugate to the hydrophobic surface, the second conjugate comprising a second bioelastic compound and a second binding compound, so that the biosensor may be reused. The second conjugate may be the same as or different from the first conjugate.

A fifth aspect of the present invention is a method for the targeted delivering of a compound in vivo to a selected region within a subject. The method comprises:

(a) administering a conjugate to the subject, the conjugate comprising the compound to be delivered and a polymer that undergoes an inverse temperature transition, wherein the polymer has a transition temperature ($T_t$) greater than the temperature at which the compound is delivered; and then (b) heating the selected region to a temperature greater than the transition temperature of the polymer, so that the compound is preferentially delivered to the selected region.

A sixth aspect of the present invention is the use of a conjugate as described above for the preparation of a medicament for the targeted delivery of a compound as described above.

The foregoing and other objects and aspects of the present invention are explained in detail in the drawings herein and the specification below.

BRIEF DESCRIPTION OF THE DRAWINGS

FIG. 6 illustrates relative SPR signal as a function of recording time of the experiment. The recording time is not identical to the experimental time, since some time segments such as flushing, buffer exchange, etc. are not included, to enhance clarity.

Assay conditions: 1 mg/ml, PBS, pH 7.2 heating rate =~1.0° C./min.

Figure 10:
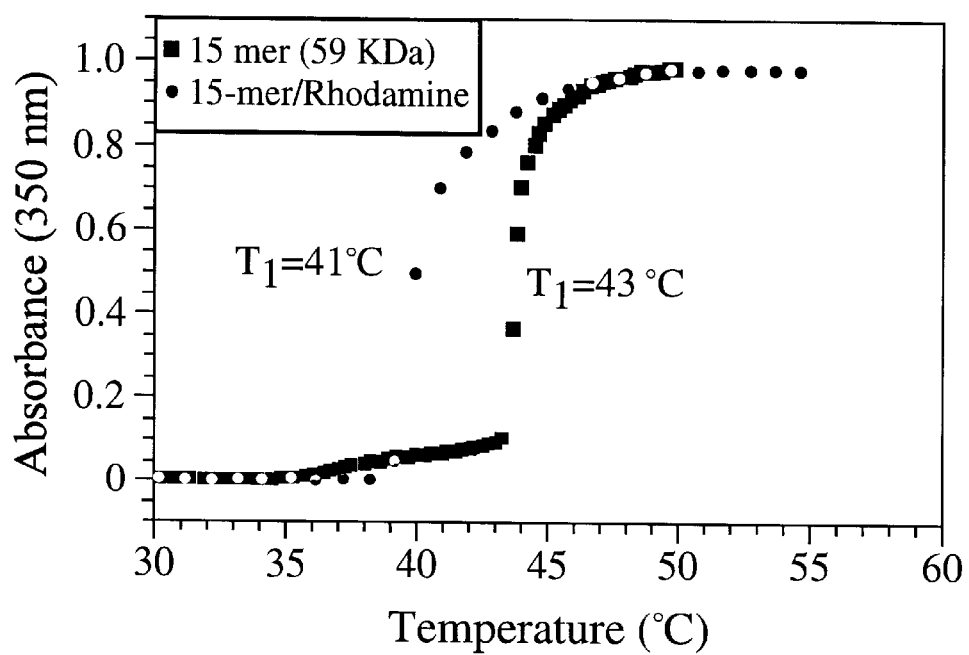

FIG. 10. Absorbance at 350 nm of the ELP 15-mer (filled squares) and Rhodamine-ELP 15 mer conjugate (filled circles) by UV-visible spectrophotometry. Assay conditions: 1 mg/ml, PBS, pH 7.2 heating rate=~1.0° C./min.

Figure 11A:
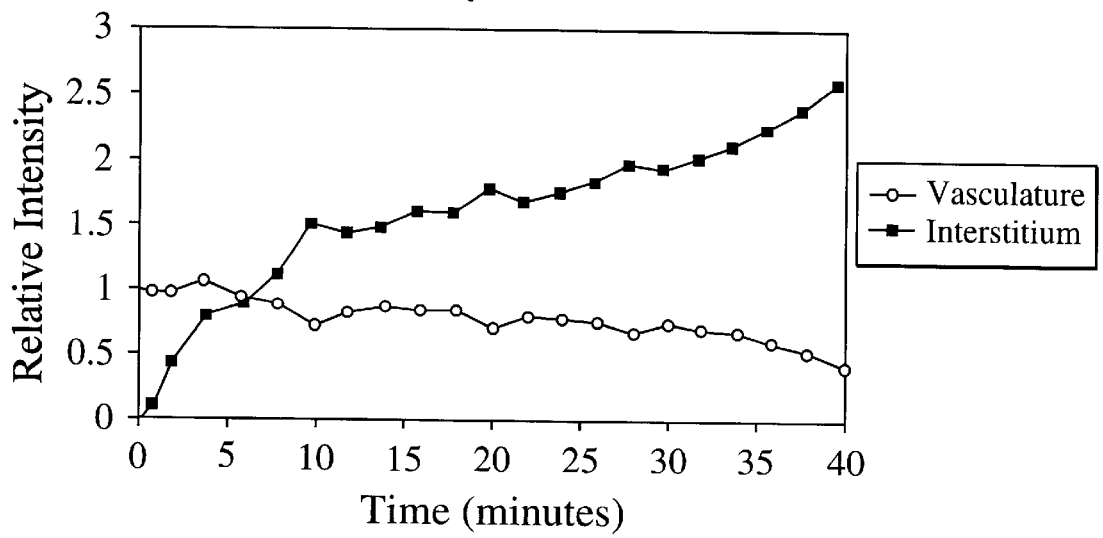

FIG. 11A. Fluorescence intensities of Rhodamine-ELP conjugate in tumor window chamber as a function of time post injection under hyperthermic conditions (42° C.). The light intensity of a representative vascular region ($I_v$) (open squares) and interstitial region ($I_i$) (filled squares) are shown normalized to the maximum vascular concentration.

Figure 11B:
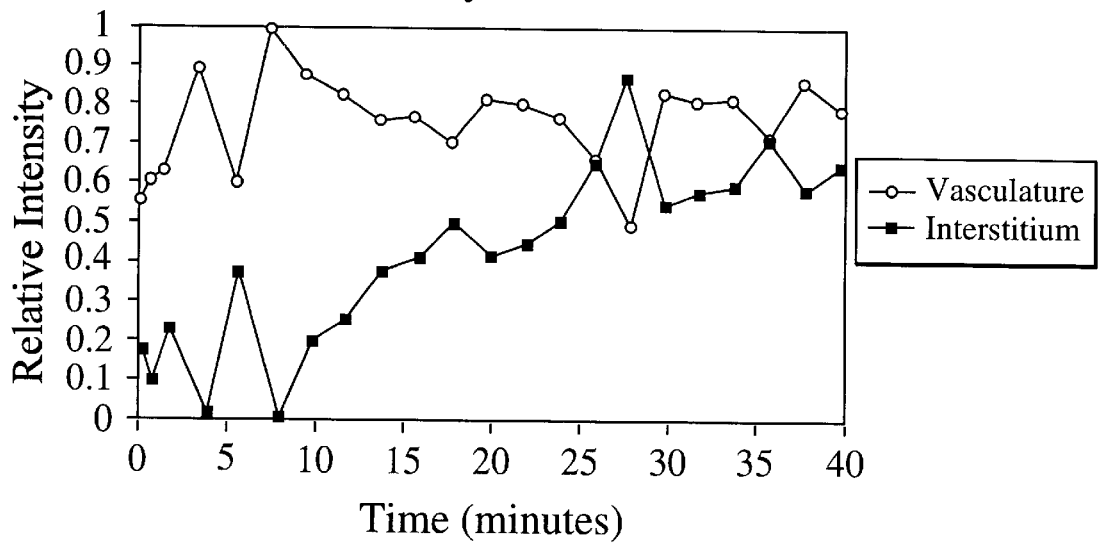

FIG. 11B. Fluorescence intensities of Rhodamine-ELP conjugate in tumor window chamber as a function of time post injection under normothermic conditions (34° C.). The light intensity of a representative vascular region ($I_v$) (open squares) and interstitial region ($I_i$) (filled squares) are shown normalized to the maximum vascular concentration.

Figure 12A:
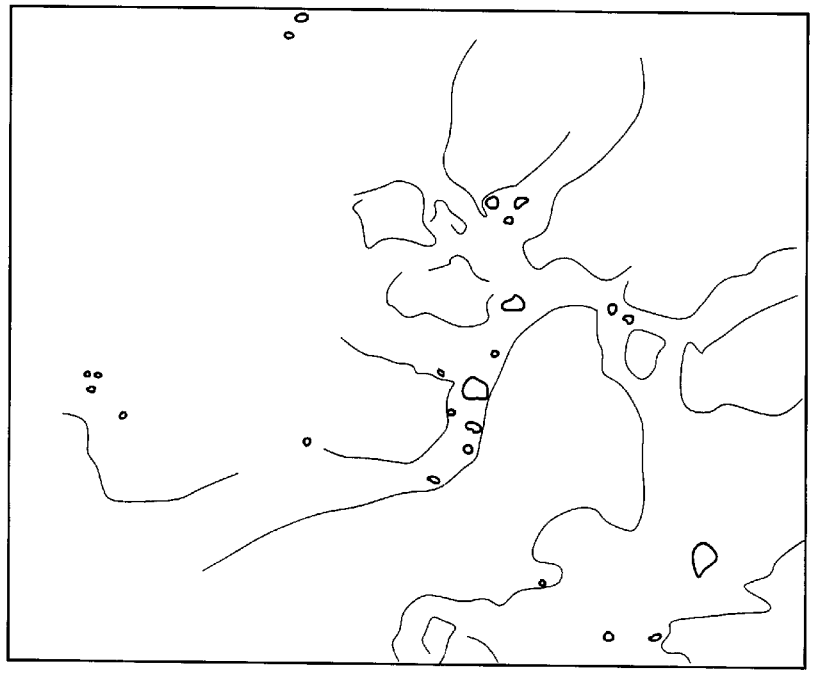

FIG. 12A shows a fluroescence image of a tumor under hyperthermic conditions (42° C.).

Figure 12B:
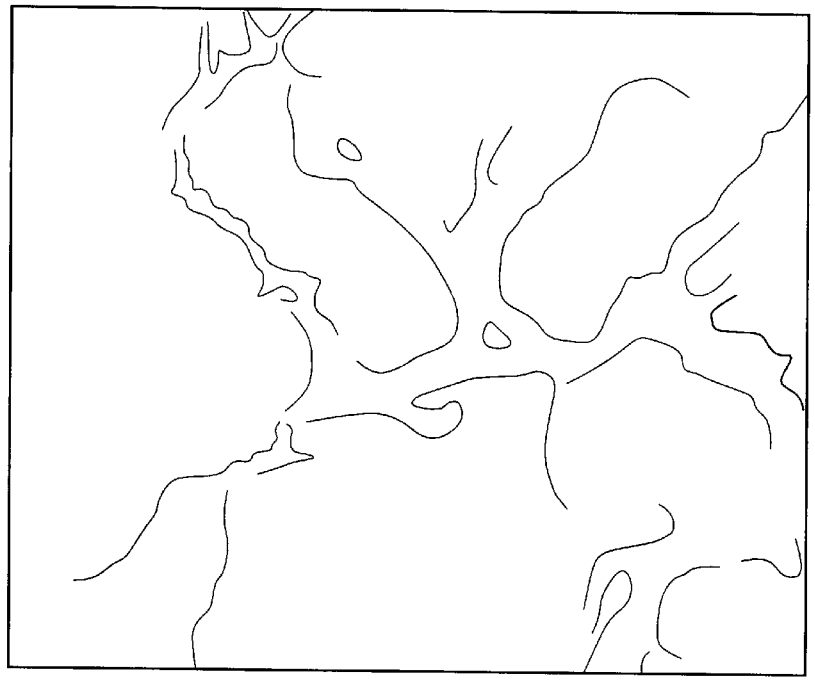

FIG. 12B shows a fluroescence image of a tumor under normothermic control (34° C.).

Figure 13:
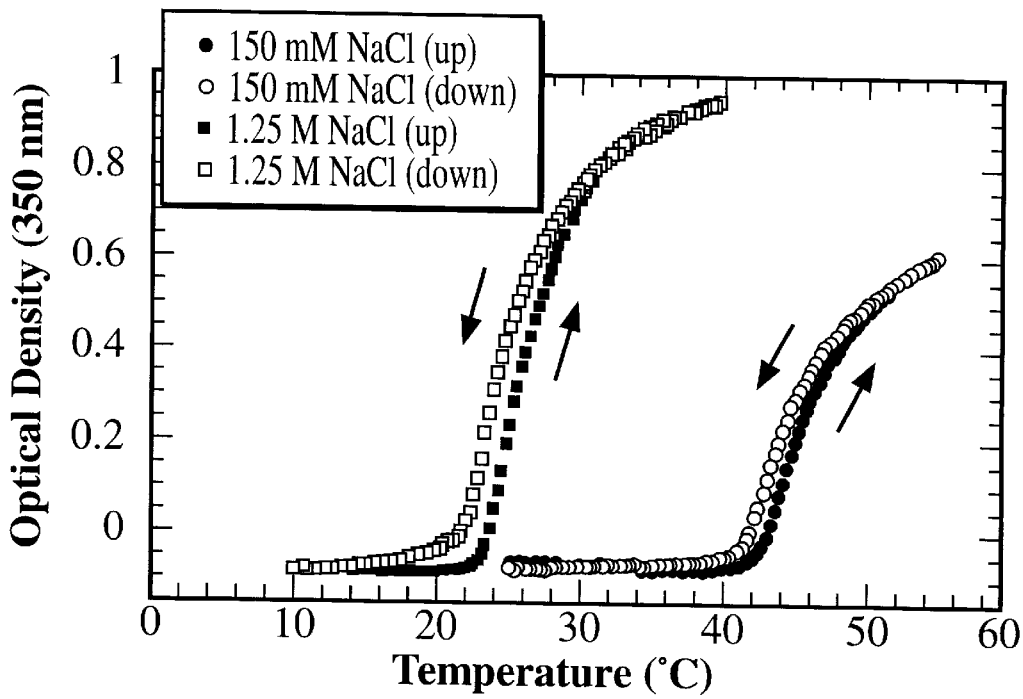

FIG. 13. Turbidity profile of 1 $\mu$M thioredoxin-ELP as a function of temperature in PBS at 150 mM NaCl and 1.25 M NaCl. The change in turbidity with increasing temperature indicates the onset of the inverse phase transition due to the formation of aggregates of the thioredoxin-ELP fusion protein. Two thermal cycles are shown in (A) (the up and down cycles are marked by arrows), showing the reversibility of the inverse phase transition. These results also show that the inverse transition can be induced isothermally at room temperature by increasing the ionic strength by the addition of NaCl.

Figure 14:
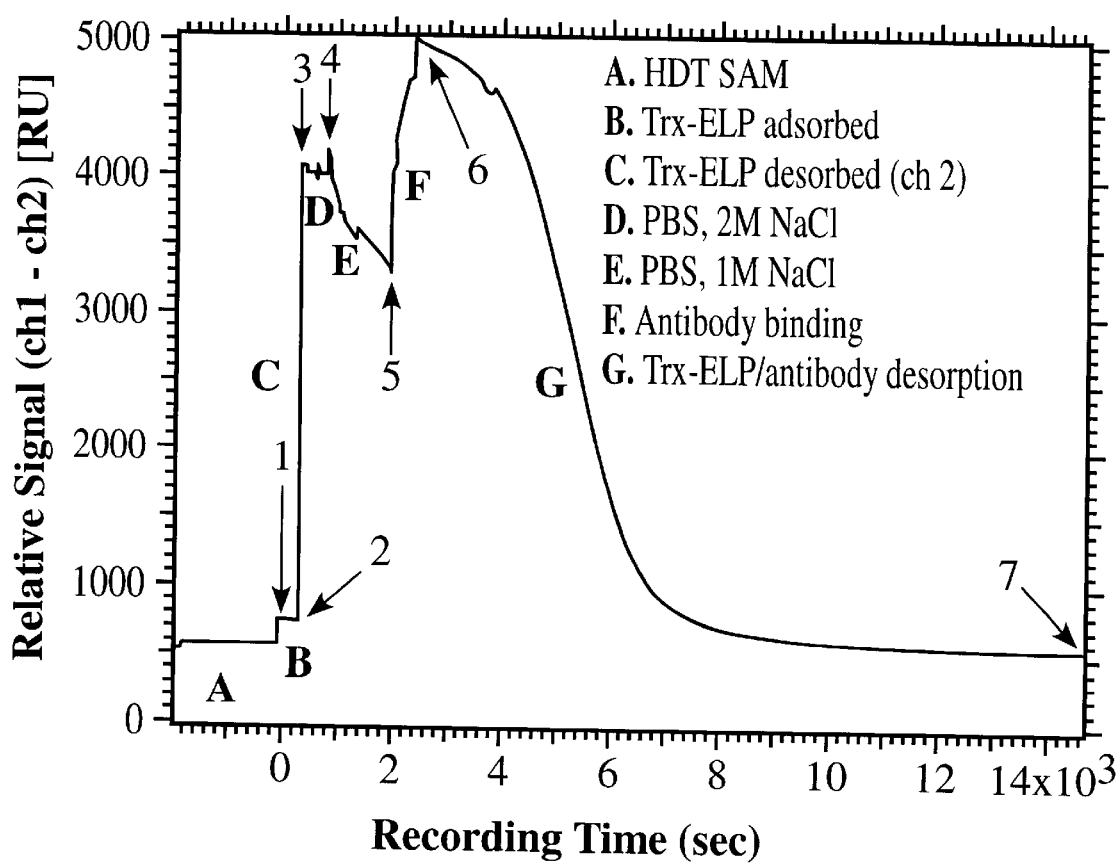

FIG. 14. Binding and desorption of a thioredoxin antibody onto the thioredoxin-ELP fusion protein, adsorbed above its $T_t$ onto a HDT SAM on gold. The relative SPR signal (channel 1–channel 2) is shown as a function of recording time of the experiment. The recording time is not identical to the experimental time, because some time segments in the SPR experiment such as flushing, buffer exchange, etc. are not included, to enhance clarity.

FIG. 15A. Adsorption of thioredoxin-ELP fusion protein on a patterned hydrophobic SAM on a hydrophilic SAM background in response to the ELP phase transition. Fluorescence microscopy of a hydrophobic patterned SAM against a hydrophilic background (40 $\mu$m wide lines of HDT against a background of MUD) incubated with Alexa488 labeled thioredoxin-ELP (1 $\mu$M in PBS) after addition of NaCl to a final concentration of 1.25 M to drive the phase transition. The sample was washed in high ionic strength buffer before imaging the sample in the same buffer.

FIG. 15B. Reversibility of the pattern upon driving the phase transition backwards. A line profile of the intensity of the fluorescence images of a patterned HDT/MUD SAM on Au after incubation of Alexa488 labeled thioredoxin-ELP fusion protein in high ionic strength (PBS+1.25 M NaCl) and after washing the patterned sample (as in (A) and whose contrast is shown by the upper line intensity profile) in low ionic strength buffer (PBS) at 4 C.

Figure 16:
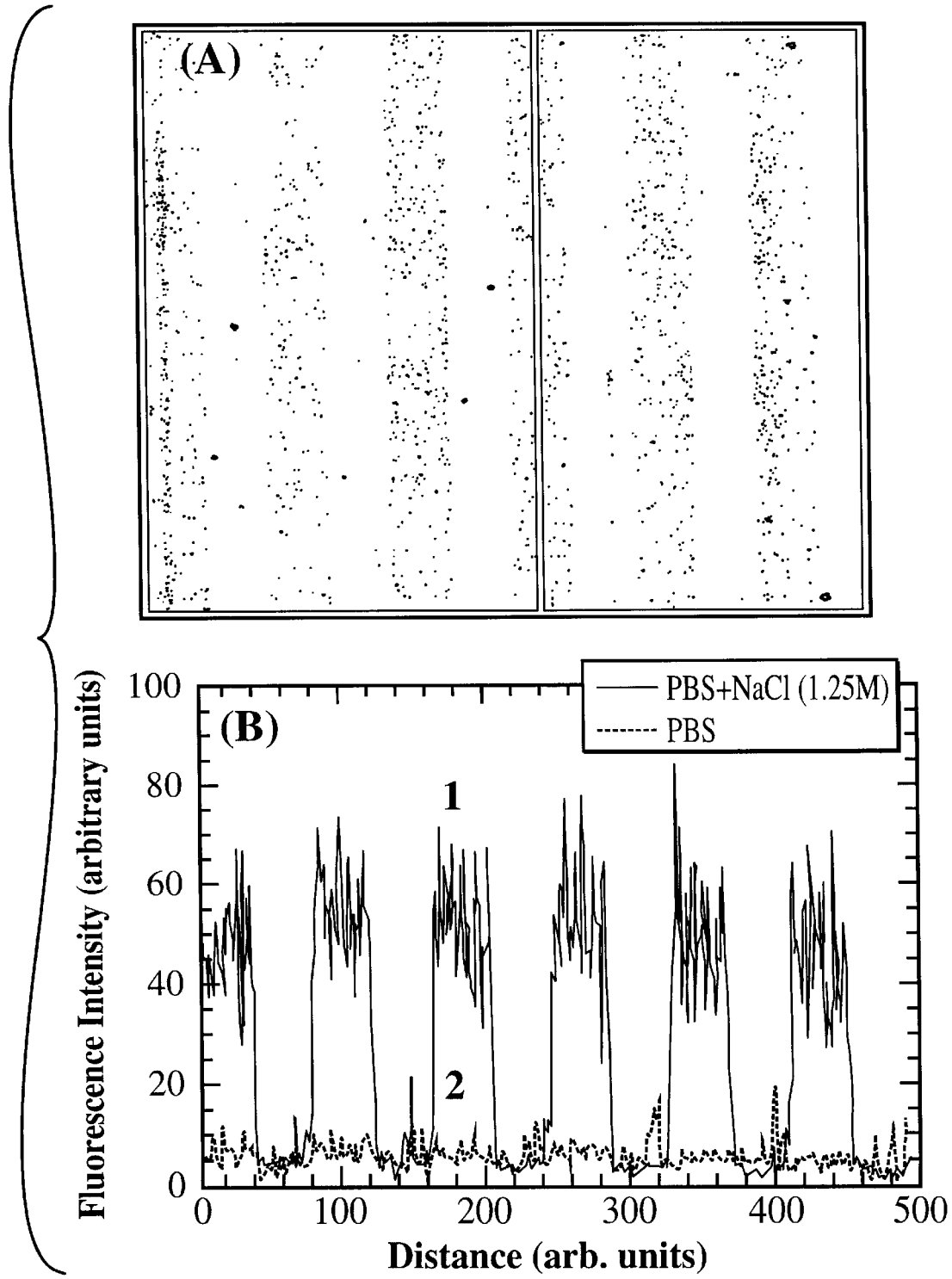

FIG. 16A. Binding of an anti-thioredoxin monoclonal antibody-FITC conjugate to a thioredoxin-ELP pattern (formed as in FIG. 3) under high ionic strength conditions, with the exception that the thioredoxin-ELP was not labeled with a fluorophore.

FIG. 16B. Reversibility of the pattern, as shown by the line profile of the fluorescence intensity of the bound antibody-FITC conjugate at 1.25 M NaCl (upper line profile) and after reversing the ELP phase transition by lowering the ionic strength and reducing the temperature to 4 C.

DETAILED DESCRIPTION OF PREFERRED EMBODIMENTS

"Compound of interest" as used herein refers to any compound, including proteins, peptides, nucleic acids particularly polynucleic acids (e.g., DNA, RNA), organic compounds, etc. Such compounds may be antibodies, receptors, ligands, hormones, drugs, etc. When the method of the invention is employed to qualitatively or quantitatively detect the compound of interest, the compound of interest may be referred to as an "analyte". The compound of interest or analyte may be carried by a cell (particularly on the surface of a cell) so that a cell (or cell of interest) is bound to the binding partner through the compound of interest.

"Binding compound" as used herein refers to a compound that specifically or selectively binds the compound of interest. In general, the binding compound and the compound of interest together comprise a specific binding pair. The binding compound may be any compound, including proteins, peptides, nucleic acids particularly polynucleic acids (e.g., DNA, RNA), organic compounds, etc. Such compounds may be antibodies, receptors, ligands, hormones, drugs, etc.

"Conjugate" as used herein refers to two moieties or functional groups that are covalently or noncovalently joined to one another, such that the two groups function together as a single structure under the conditions of the methods described herein. In one embodiment, the conjugate is a fusion protein. The binding compound may be carried by (e.g., on the surface of) a cell, which cell is coupled to the polymer that undergoes an inverse temperature transition through an antibody or other binding partner with the cell.

"Fusion protein" as used herein refers to a protein or peptide, produced by recombinant means (i.e., expression from a nucleic acid) that is comprised of a first protein or peptide covalently joined on expression to a second protein or peptide.

A "polymer that undergoes an inverse temperature transition" herein refers to a polymer that is soluble in an aqueous solution at a lower temperature, and is insoluble in an aqueous solution at a higher temperature.

"Transition temperature" or "$T_t$" as used herein, refers to the temperature above which a polymer that undergoes an inverse temperature transition is insoluble in an aqueous system (e.g., water, physiological saline solution), and below which such a polymer is soluble in an aqueous system. Preferred $T_t$s for in vitro applications of the invention are 0° or 20° to 60° or 100° C.; preferred $T_t$s for in vivo applications are 35° to 45° C.

A "bioelastic polymer" is, in general, a polypeptide that exhibits an inverse temperature transition. Bioelastic polymers are discussed in greater detail below.

"Poly(N-isopropylacrylamide) polymer" as used herein refers to a class of polymers, including copolymers thereof, that exhibit an inverse temperature transition. The polymers are formed of at least N-isopropylacrylamide, and may include other monomers that polymerize therewith, such as acrylamide (Aam), methacrylamide, propylacrylamide, butylacrylamide, acrylate, methacrylate, etc.

1. Bioelastic Polymers

Bioelastic polymers are, in general, polypeptides that comprise repeating units that form beta-turns. A beta-turn is a 10 atom hydrogen-bonded. ring in which the C=O of amino acid residue i is hydrogen-bonded to the NH residue of amino acid i+3. Repetitive beta-turns result in elastic beta-spiral structures. Bioelastic polymers, in general, are soluble in water at a sufficiently low temperature, but hydrophobically fold and associate to form a separate phase as the temperature is raised through the transition temperature. When more hydrophobic amino acids are included in the bioelastic polymer the transition temperature is lower; when fewer hydrophobic amino acids are included in the bioelastic polymer the transition temperature is greater. The phase transition can occur reversibly or irreversibly upon raising the temperature. The chain length of the bioelastic polymer is not critical, but typically is from 10 or 20 to 50, 100, 200, or 1000 or more amino acids. Numerous bioelastic polymers are known and described in, for example, U.S. Pat. Nos. 4,132,746; 4,187,852; 4,589,822; 4,870,055; and 5,064,430 (applicants specifically intend that the disclosures of all patent references cited herein be incorporated herein by reference in their entirety). A particularly preferred bioelastic polymer is one that contains the elastin repeat: (Val-Pro-Gly-X-Gly)$_n$ or (VPGXG)$_n$ (SEQ ID NO. 1), where n is from 2, 3 or 4 to 10, 20, 30 40, 100 or 200 or more, and X is any amino acid, such as valine, alanine or glycine, with X being the same or different in each repeat unit of the polypeptide chain (that is, X may be a combination of different amino acids, in various ratios).

2. Separation and Immunoassay Systems

As noted above, the present invention provides a method of binding a compound of interest in an aqueous solution, the method comprising the steps of:

(a) providing a conjugate comprising a bioelastic compound and a binding compound, wherein the binding compound specifically binds the compound of interest, and wherein the bioelastic compound has a transition temperature below which the bioelastic compound is soluble in the solution, and above which the bioelastic compound is insoluble in the solution;

(b) contacting the conjugate to the compound of interest in an aqueous solution so that the compound binds thereto, with the contacting step carried out at a temperature below the transition temperature of the bioelastic compound; and then (c) raising the temperature of the conjugate to a temperature above the transition temperature of the bioelastic compound so that the conjugate separates from the aqueous solution with the compound of interest bound thereto.

As noted above, the binding compound may be any suitable molecule, such as a protein or peptide. The binding compound may be an antibody. Likewise, the compound of interest, may be a protein or peptide such as an antibody.

When the method is used as an immunoassay, the compound of interest is referred to as an analyte, and the binding step is followed by the step of detecting the analyte. Typically, but not in all cases, either the binding compound or the analyte is an antibody in an immunoassay. How detection of the analyte is carried out is not critical and will depend upon the particular immunoassay format. The present invention can be implemented with any immunoassay format, including direct immunoassays, indirect immunoassays, and sandwich assays; and heterogeneous or homogeneous immunoassays, numerous variations of which are known to persons skilled in the art.

3. Biosensor Systems and Biosensor Regeneration

As also noted above, the present invention provides an article useful as a regenerable biosensor for binding a compound of interest from an aqueous solution, the article comprising:

(a) a solid support having a hydrophobic surface formed thereon; and (b) a conjugate reversibly bonded to the hydrophobic surface, the conjugate comprising (i) a bioelastic compound and a (ii) binding compound, wherein the binding compound specifically binds the compound of interest, and wherein the bioelastic compound has a transition temperature below which the bioelastic compound is soluble in the solution, and above which the bioelastic compound is insoluble in the solution; so that the biosensor may be used to bind the compound of interest at a temperature above the transition temperature, and so that the conjugate can be removed from the solid support for recycling of the article by lowering the temperature of the solid support (or the solution in which the solid support is carried, so long as the temperature of the bioelastic compound is lowered)

below the transition temperature. Again, the binding compound may be a protein or peptide, such as an antibody, and the compound of interest may be a protein or peptide, such as an antibody.

The present invention can be utilized with any type of biosensor where it is desirable to regenerate a solid support that has a binding compound immobilized thereon. For example, the present invention may be utilized with optical biosensors such as described in U.S. Pat. Nos. 5,313,264 to Ulf et al., 5,846,842 to Herron et al., 5,496,701 to Pollard-Knight et al., etc. The present invention may be utilized with potentiometric or electrochemical biosensors, such as described in U.S. Pat. No. 5,413,690 to Kost, or PCT Application WO98/35232 to Fowlkes and Thorp. The present invention may be utilized with a diamond film biosensor, such as described in U.S. Pat. No. 5,777,372 to Kobashi. Thus, the solid support may be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. For example, the solid support may be comprised of polyethylene, polytetrafluoroethylene, gold, silicon, silicon oxide, silicon oxynitride, indium, platinum, iridium, indium tin oxide, diamond or diamond-like film, etc. When the solid support does not inherently provide a hydrophobic surface to which the bioelastic polymer may reversibly bind (i.e., non-covalently, primarily by means of hydrophobic interactions), the surface may be functionalized or coated to render it hydrophobic in accordance with any of a variety of standard techniques.

The present invention may be utilized with different binding compounds or compounds of interested are desired to be bound to a substrate, for the high throughput screening of molecular interactions, such as in "chip-based" and "pin-based" combinatorial chemistry techniques, and can be prepared by modification of known techniques based on the disclosure provided herein. In such case the substrate or solid support has a surface portion, with the surface portion comprising a plurality of discrete known regions (each of which has a hydrophobic surface portion formed thereon). A plurality of different conjugates (differing in the binding compound, and optionally in the bioelastic compound thereof) are bound to the surface portion, with different conjugates positioned on the surface portion in different ones of the discrete known regions. All can be prepared in accordance with known techniques. See. e.g., U.S. Pat. No. 5,445,934 to Fodor et al., U.S. Pat. No. 5,288,514 to Ellman, and U.S. Pat. No. 5,624,711 to Sundberg et al., the disclosures of which are incorporated by reference herein in their entirety.

Thus the present invention provides a method of recycling a biosensor as described above by:

(a) providing a biosensor comprising a solid support having a hydrophobic surface formed thereon and a first conjugate reversibly bonded to the hydrophobic surface, the conjugate comprising (i) a bioelastic compound and (ii) a binding compound, wherein the binding compound has the compound of interest specifically bound thereto, and wherein the bioelastic compound has a transition temperature below which the bioelastic compound is soluble in the solution, and above which the bioelastic compound is insoluble in the solution; and then (b) separating the conjugate with the compound of interest bound thereto from the solid support by lowering the temperature of the biosensor (or the solution in which the sensor is carried, so long as the temperature of the bioelastic compound is lowered) to below the transition temperature; and then (c) binding a second conjugate to the hydrophobic surface, the second conjugate comprising a second bioelastic compound and a second binding compound, so that the biosensor may be reused. Again, the second conjugate may be the same or different from the first conjugate, and either or both of the second bioelastic compound and second binding compound may be different from the first.

4. Targeted Delivery of Therapeutics to Solid Tumors by Thermally-Responsive Polymers As discussed above, a method for the targeted delivering of a compound in vivo to a selected region within a subject comprises: (a) administering a conjugate to the subject, the conjugate comprising the compound to be delivered and a polymer that undergoes an inverse temperature transition, wherein the polymer has a transition temperature ($T_t$) greater than the temperature at which the compound is delivered; and then (b) heating the selected region to a temperature greater than the transition temperature of the polymer, so that the compound is preferentially delivered to the selected region. The polymer may be a bioelastic polymer as described above, or may be a poly(N-isopropylacrylamide) polymer as described above.

While the present invention is concerned primarily with the treatment of human subjects, the invention may also be used for the treatment of animal subjects, particularly mammalian subjects such as dogs, cats, horses, cows, pigs, etc., for veterinary purposes.

Administering of the conjugate to the subject may be carried out by any suitable means, such as subcutaneous injection, intraperitoneal injection, intraveneous injection, intramuscular injection, oral administration, inhalation administration, transdermal administration, etc. Preferred administration techniques are typically "systemic" in that a particular region of interest is not specifically targeted.

The selected region may be any suitable target or portion of the subject's body, such as a limb, organ, or other tissue or tissue portion. The selected region may be comprised of hyperproliferative tissue which may be malignant or non-malignant, such as a solid tumor). Examples of tumors, cancers and neoplastic tissue that can be treated by the present invention include but are not limited to malignant disorders such as breast cancers; osteosarcomas; angiosarcomas; fibrosarcomas and other sarcomas; leukemias; lymphomas; sinus tumors; ovarian, uretal, bladder, prostate and other genitourinary cancers; colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas. Examples of premalignant and nonneoplastic hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; etc.

Heating of the selected region may be carried out by any means, such as by application of an heat source e.g. a heat pad, a hot water bath, infrared heating lamps, etc., or by heating means such as directing microwave, ultrasound or other radio frequency energy at the selected region, etc.

Any suitable compound for which targeted delivery is desired may be administered by this means, including imaging agents (or contrast agents) and therapeutic agents.

In a preferred embodiment, the therapeutic agent is a radionuclide. Any radionuclide, whether it be for therapeutic or imaging purposes, may be employed, including but not limited to, $^{131}$I, $^{90}$Y $^{211}$At, $^{212}$Bi, $^{67}$Cu, $^{186}$Re, $^{188}$Re, and $^{212}$Pb.

The therapeutic agent may be a chemotherapeutic agent or cytotoxic agent. Examples of chemotherapeutic agents which may be coupled to the conjugate include, but are not limited to, methotrexate, adriamycin, doxorubicin, taxol, etc. Examples of cytotoxic agents which may be coupled to the conjugate include, but are not limited to, ricin, (or more particularly the ricin A chain).

Imaging agents may be fluorescent compounds such as rhodamine or green fluorescent protein (GFP) or a radionuclide such as $^{111}$In.

Coupling of conjugates may be carried out by any suitable means, such as by recombinant means where elastin is joined to a protein or peptide such as GFP; by chemical means where the compound to be coupled to the polymer is a small molecule; or by enzymatic coupling.

The conjugates (or "active compounds") described above may be formulated for administration in a single pharmaceutical carrier or in separate pharmaceutical carriers for the treatment of a variety of conditions. In the manufacture of a pharmaceutical formulation according to the invention, the active compounds including the physiologically acceptable salts thereof, or the acid derivatives of either thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

The therapeutically effective dosage of any one active agent, the use of which is in the scope of present invention, will vary somewhat from compound to compound, patient to patient, and will depend upon factors such as the condition of the patient and the route of delivery. Such dosages can be determined in accordance with routine pharmacological procedures known to those skilled in the art, particularly in light of the disclosure provided herein. In one example, the dosage is from 1 to 10 micrograms of active compound per Kilogram subject body weight.

In another example, where the therapeutic agent is $^{131}$I, the dosage to the patient is typically from 10 mCi to 100, 300 or even 500 mCi. Stated otherwise, where the therapeutic agent is $^{131}$I, the dosage to the patient is typically from 5,000 Rads to 100,000 Rads (preferably at least 13,000 Rads, or even at least 50,000 Rads). Doses for other radionuclides are typically selected so that the tumoricidal dosae is equivalent to the foregoing range for $^{131}$I. cl 5. Thermodvnamically Addressable Reversible Adsorption of Peptides (TRAP)

Patterned biomolecules on surfaces have applications ranging from modulation of cell-substrate interactions in biomaterials and tissue engineering, to the fabrication of multi-analyte biosensors, clinical assays, and genomic and proteomic arrays. Many methods exist to pattern biomolecules on different substrates, such as metals, polymers, glass and self-assembled monolayers (SAMs). Patterned SAMs, which can be fabricated by photolithography, micromachining, microwriting, and microcontact printing ($\mu$CP), are convenient molecular templates for protein patterning on gold and silicon oxide substrates. A number of other methods such as electrochemical patterning of SAMs on gold, direct protein microstamping (also called $\mu$CP) and reactive microcntact printing onto SAMs and activated polymer surfaces have also been recently applied to pattern proteins at the micrometer scale.

A primary limitation of many current patterning methods is the lack of temporal control over the patterns. Most current protein patterning methods result in static patterns, i.e., patterns that cannot be dynamically controlled or modulated after fabrication. There are several possible solutions to the problem of creating dynamic protein patterns. The first approach is to create "smart" patterned templates—surfaces whose reactivity can be turned on at specific times—to subsequently allow dynamic presentation of ligands and immobilization of proteins. In one example, Mrksich and coworkers have synthesized electroactive SAMS which release attached groups when an electrical potential is applied to the gold. More recently, they have shown that the reactivity of SAMs presenting a terminal quinone-moiety can be chemically or electrochemically modulated, and that a protein can be specifically immobilized on these electroactive, dynamic SAMs. The extension of this method to create dynamic protein patterns on these "smart" SAMs, still remains to be achieved.

This application describes a different approach to directly modulate the interaction between a patterned surface and a protein to create dynamic protein patterns. This method involves extrinsic control of the hydrophobic interaction between a protein and a surface template that contains hydrophobic patterns against a protein-resistant hydrophilic background. In one example embodiment (Example 5 below), we have imparted environmentally triggered, reversible hydrophobicity to a model protein, thioredoxin, by fusing it to an elastin-like polypeptide (ELP).

A further aspect of the present invention is, accordingly, an article having a regenerable patterned surface for binding compounds of interest from an aqueous solution, the article comprising:(a) a solid support having a plurality of separate and discrete hydrophobic surfaces formed thereon; and (b) a conjugate (e.g., a fusion protein) reversibly bonded to each of the separate and discrete hydrophobic surfaces, the conjugate comprising (i) a bioelastic compound and (ii) a binding compound (e.g., a protein or peptide), wherein the binding compound specifically binds a compound of interest, and wherein the bioelastic compound has a transition temperature below which the bioelastic compound is soluble in the solution, and above which the bioelastic compound is insoluble in the solution; so that the surfaces may be used to bind a compound of interest at a temperature above the transition temperature, and so that the conjugate can be removed from the hydrophobic surface for recycling of the article by lowering the temperature of the solid support below the transition temperature. Preferably, the separate and discrete hydrophobic surfaces are separated by a hydrophilic surface.

In one preferred embodiment, conjugates bound to different ones of the separate and discrete hydrophobic surfaces have different bioelastic compounds, so that different conjugates may be removed from hydrophobic surfaces with different release conditions. Any release conditions may be employed, including but not limited to change in temperature, ionic strength, pH, chemical or biochemical modification, or binding of the ligand to sequences within an elastin that alter the transition temperature and thereby induce the transition isothermally.

In a preferred embodiment, conjugates bound to different ones of the separate and discrete hydrophobic surfaces have different binding compounds, so that different compounds of interest are selectively bound at different ones of the separate and discrete hydrophobic surfaces.

Any suitable binding compound may be employed, such as an antibody. Any suitable compound of interest may be employed, including but not limited to proteins and peptides (e.g., an antibody).

The solid support may comprise a polymer, a metal such as gold, a semiconductor, and combinations thereof.

Further, a method of recycling a used article that has a patterned surface to which has been bound at least one compound of interest, comprises (a) providing an article as described above, and (b) separating the conjugate from each of the separate and discrete hydrophobic surfaces by lowering the temperature of the biosensor to below the transition temperature. The method may further comprise the step of (c) binding a second conjugate to each of the separate and discrete hydrophobic surfaces, the second conjugate comprising a second bioelastic compound and a second binding compound, so that the biosensor may be reused. The first conjugates and the second conjugates replaced at each of the separate and discrete hydrophobic surfaces may be the same or different. In addition, individual ones of the conjugates may be released (and optionally replaced), as where conjugates bound to different ones of the separate and discrete hydrophobic surfaces each have a different bioelastic compound, so that different ones of the conjugates may be removed from different hydrophobic surfaces with different release conditions.

The present invention is explained in greater detail in the following non-limiting Examples.

EXAMPLE 1

Production of a Thioredoxin-ELP Fusion Protein and Poly-NIPAAm/Am Copolymer

Gene Synthesis. The synthetic gene for the ELP-1 mer was constructed from four 5'-phosphorylated, PAGE purified synthetic oligonucleotides (Integrated DNA Technologies, Inc.), ranging in size from 86 to 97 bases. The oligonucleotides were annealed (100 pmol of each oligonucleotide in 50 µl ligase buffer, NEB Inc.) to form double-stranded DNA spanning the ELP gene with EcoRI and HindIII compatible ends. The annealed oligonucleotides (2 pmol) were then ligated using T4 DNA ligase (10:1 insert:vector molar ratio) into EcoRI-HindIII linearized and dephosphorylated pUC-19 (NEB, Inc.). Chemically competent E. Coli XL1-Blue cells were then transformed with the ligation mixture, and incubated on ampicillin-containing agar plates. Colonies were initially screened by blue-white screening, and subsequently by colony PCR to verify the presence of an insert. The DNA sequence of a putative insert was verified by automated fluorescent DNA sequencing (ABI 373 DNA Sequencer).

Gene Oligomerization. First, a 2-mer was created by ligating a 1-mer into a vector containing a 1-mer insert. This process was repeated to create a library of mers ranging from 2 to 9-mer. For a typical oligomerization, the vector was linearized with PflMI, and enzymatically dephosphorylated. The insert was doubly digested with PflMI and BglII, purified by agarose gel electrophoresis (Qiaex II Gel Extraction Kit, Qiagen Inc.), ligated into the linearized vector with T4 DNA ligase at a 5:1 insert:vector molar ratio, and transformed into chemically competent E. coli XL1-Blue cells. Transformants were screened by colony PCR, and oligomerization of the 2-mer and 3-mer was further confirmed by DNA sequencing. Standard molecular biology protocols were used for gene synthesis and oligomerization (F. Ausubel et al., Current Protocols in Molecular Biology (John Wiley & Sons 1995)).

Protein Expression. The genes were subcloned from pUC-19 into a modified expression vector derived from pET-32b (Novagen Inc.). After confirmation of successful cloning by colony PCR and DNA sequencing, pET-32b containing the ELP insert were transformed into the expression strain, BLR21(DE3) (Novagen, Inc.). 2×YT media, supplemented with 100 µg/ml ampicillin, were inoculated with transformed cells, incubated at 37° C. with shaking (250 rpm), and induced at an $OD_{600}$ of 0.6 by the addition of isopropyl α-thiogalactopyranoside (IPTG) to a final concentration of 1 mM. The culture were incubated an additional 3 hours, harvested by centrifugation at 4° C., resuspended in water. and lysed by ultrasonic disruption at 4° C. Soluble and insoluble fractions of the cell lysate were then characterized by sodium-dodecyl sulfate polyacrylamide gel electrophoresis (SDS-PAGE) (U. Lammli, *Nature* 227: 680 (1971).

Figure 1:
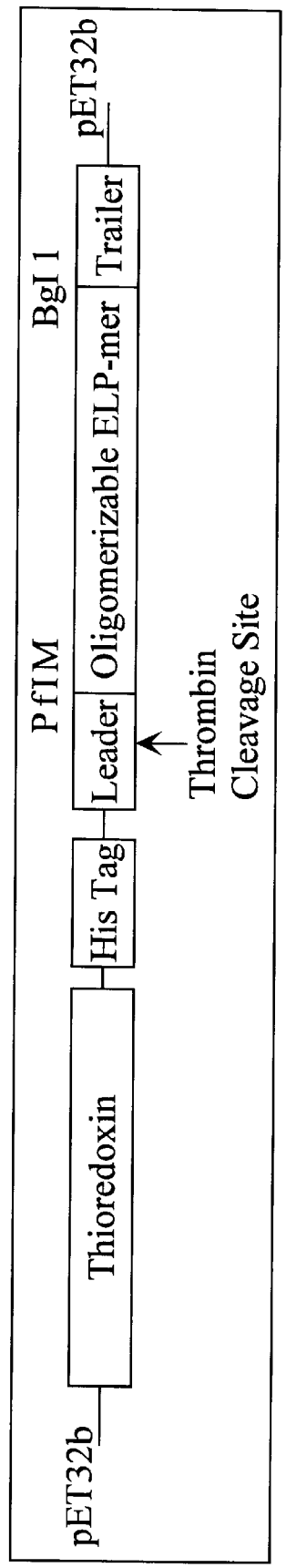
FIG. 1 illustrates the Expression construct in pET-32b, which includes two N-terminal domains: thioredoxin, and a (HiS)$_6$ tag.

ELP Expression and Purification. The ELP of interest was expressed as a C-terminal fusion, with thioredoxin and a $(His)_6$ tag at the N-terminus with an intervening thrombin cleavage site (FIG. 1). The fusion protein was initially purified by immobilized metal ion affinity chromatography (IMAC) using a Nickel-chelating nitrilotriacetic derivatized resin (Novagen Inc.) (J. Porath, *Prot. Expr. Purif.* 3: 262 (1992). Alternatively, the fusion protein was purified by repeated cycles of thermal- or salt-induced aggregation, followed by centrifugation, and resolubilization under conditions of low salt or temperature such that the solution temperature was below the inverse transition of the ELP fusion protein. After purification, the soluble ELP-thioredoxin fusion was cleaved by incubation with thrombin, and the ELP was purified by salt-or temperature cycling.

Synthesis and Characterization of Poly(NIPAAm) copolymer. The $T_t$ of poly(NIPAAm) can be adjusted by copolymerizing NIPAAm with acrylamide homologs. Based on previous studies which have reported on this effect (C. Chiklis and J. Grasshof, *J. Polym. Sci. Part* A-2 8: 1617 (1970); L. Taylor and L. Cerankowski, *J. Polym. Sci. Polym. Chem.* 13: 2551 (1975)), we synthesized ~3 g. of an amine-terminated poly(NIPAAm/AAm) copolymer containing 16.6 mol% AAm by free radical copolymerization of NIPAAm and AAm in methanol at 60° C. for 20 h using 1 mmol % of 2, 2'-azobisbutyronitrile (AIBN) as initiator and 1 mmol % of 2-aminoethanethiol hydrochloride (AET) as chain transfer agent. (Y. Takei et al., *Bioconj. Chem.* 4: 42 (1993). The copolymer was purified by precipitating the reaction solution into diethyl ether and dried under vacuum. The molecular weight distribution of this copolymer was determined by gel permeation chromatography using monodisperse poly(ethylene glycol) standards to calibrate the MW. The polymer has a weight average MW of 20,800 Da and a polydispersity of 2.28.

Inverse Transition Temperature. The optical absorbance at 500 nm of the ELP biopolymer or poly(NIPAAm/AAm) copolymer was monitored in the 4–80° C. range on a Shimadzu-2001 UV-visible spectrophotometer, equipped with a water-jacketed optical cell connected to a recirculating water bath. The $T_t$ was determined from the midpoint of the change in optical absorbance at 350 nm due to aggregation of ELP or ELP-thioredoxin fusion protein as a function of temperature at a heating or cooling rate of 1.3° C. $min^{-1}$.

EXAMPLE 2

Immunoassay with a Thioredoxin-ELP Fusion Protein

Immunoassays are commonly used to detect analytes such as enzymes, hormones, drugs, and other molecules of interest in complex biological mixtures. By definition, an immunoassay relies on the specific binding of an antigen by an antibody, but assays using other biological high affinity binding partners (e.g., ligand-cell surface receptor, inhibitor-enzyme, etc.) can also be employed in an analogous manner. A number of different immunoassay formats have been developed to detect and/or quantitate the levels of analytes; for a review of immunoassays, see PCT Patent Application WO 86/06492.

Here we report an immunoassay in which one of the reactants (e.g., either the antigen or the antibody) is genetically fused to an elastin-like polypeptide (ELP), which we define as oligomeric polypeptides composed of the pentapeptide repeat Val-Pro-Gly-X-Gly (where X, the guest residue, can be any amino acid). ELPs undergo a reversible phase transition. Below the transition temperature $(T_t)$, the polypeptide is highly soluble in aqueous solution; But when the solution temperature is raised above the $T_t$, the transition occurs, resulting in aggregation of the polypeptide and partitioning from solution to form a coacervate phase. The aggregated polypeptide can then be easily and selectively precipitated from solution by centrifugation or ultrafiltration. The precipitation is thermally reversible, and upon subsequently resuspending the precipitated polypeptide in an aqueous solution at a temperature below the $T_t$, the precipitate completely redissolves. The transition is also sharp, taking place over a 1–2° C. range, and can be designed to occur at any temperature between 0 and 100° C. by precisely specifying the guest residue sequence and chain length of the ELP polypeptide, variables that can be exquisitely controlled at the gene level.

In the assay reported here, the reactants were thioredoxin, a soluble *E. coli* protein, and an anti-thioredoxin mouse antibody. A competitive binding assay was developed in which known amounts of fluorophore-labeled antibody and thioredoxin-ELP fusion protein were incubated with unknown amounts of the analyte (unlabeled antibody), followed by thermally-induced capture of the complex and spectrofluorimetric analysis.

One strength of this immunoassay method is that the ELP is fused to the reactant genetically rather than by chemical conjugation. This is achieved by joining a gene encoding the polypeptide sequence to a gene of the reactant protein using the techniques of molecular biology. The reactant could be a protein antigen, an antibody or antibody fragment, an enzyme inhibitor, a receptor, or any other protein in an affinity pair of interest. Once constructed, the fused gene can be used in protein expression systems to produce the ELP-fused immunoassay reactant.

A. Materials and Methods

Synthesis of the ELP Gene. A gene encoding a 50 amino acid sequence was constructed from chemically-synthesized oligonucleotides (Integrated DNA Technologies, Inc.) using standard molecular biology protocols. The 50 amino acid sequence contained 10 repeats of the pentapeptide VPGXG, where the guest residues (V, A, and G in a 5:2:3 molar ratio) were selected to provide in a $T_t$ of 40C. The gene was oligomerized end-to-end 15 times by standard molecular biology techniques, to produce an oligomeric ELP gene encoding a 750 residue polypeptide.

Production of Thioredoxin/ELP Fusion. The DNA sequence of pET-32b (Novagen, Inc.), an expression plasmid containing a gene for thioredoxin, was modified to include a Sfi I restriction site, which permitted insertion of the ELP gene downstream of the thioredoxin gene. The modified plasmid, containing the gene sequence for a thioredoxin-ELP fusion, was transformed into the *E. coli* strain BLR(DE3) (Novagen Inc.). Shaker flask cultures of the transformed cells were incubated at 37° C. to mid-log phase ($A_{600}$=0.800). Protein expression was then induced with 1 mM IPTG, and the cultures were incubated for a further 3 hours. Cells were lysed by ultrasonication, and the soluble fusion protein was purified from cell lysate by thermally-induced aggregation of the thioredoxin-ELP fusion protein, followed by centrifugation. The fusion protein was subsequently resolubilized in cold buffer at a temperature below the $T_t$. Protein purity was ascertained by SDS-PAGE, and protein concentration was determined spetrophotometrically (UV-1601, Shimadzu Corp.). Anti-Thioredoxin Antibody Preparation. A mouse IgG monoclonal anti-thioredoxin antibody (gift of David Huston, Baylor College of Medicine) was conjugated to fluoroscein-5-isothiocyanate (FITC) (Molecular Probes, Inc.). Labeled antibody was then separated from unreacted FITC by gel filtration on a Sephadex G-25 column (Pharmacia, Inc.). The concentration of antibody was determined spectrophotometrically and by BCA total protein. assay (Pierce Chemical Company). The fluorophore to protein ratio in the FITC-labeled antibody was approximately 3.0.

Immunoassay. FITC-labeled antibody and thioredoxin-ELP were each added to a concentration of 0.5 $\mu$M in 50 $\mu$l PBS. Free ELP (without fused thioredoxin) was also added to a final concentration of 15 $\mu$M to facilitate precipitation of the antibody-thioredoxin/ELP complex. Unlabeled antibody (the analyte) was added to the assay mixture in varying amounts, with final concentrations ranging from 5 nM to 5 $\mu$M. The analyte-antibody mixtures were incubated at 37 C for 1 hour, then heated to 48° C. for five minutes to induce the ELP phase transition, and then centrifuged warm (T>45° C.) for 10 minutes at 16,000 g. The supernatant was removed, and the pellet was resuspended in cold PBS. The fluorescence (excitation$_{max}$=494 nm, emission$_{max}$=519 nm) of both the supernatant and the resolubilized precipitate were determined by spectrofluorimetry (SLM-Aminco Inc.).

B. Results and Discussion

Figure 2:
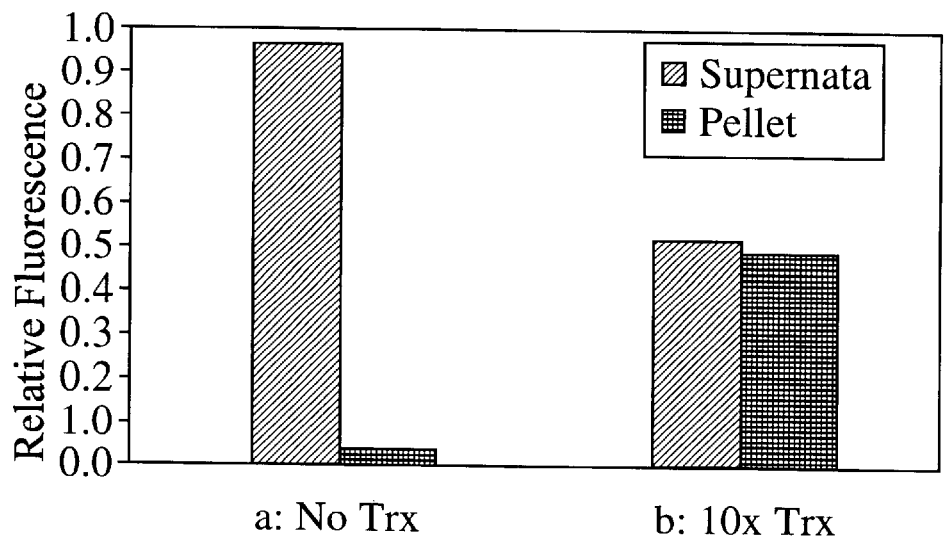
FIG. 2a illustrates an immunoassay with no thioredoxin-ELP (and hence no specific antibody capture)
FIG. 2b illustrates an immunoassay with 10:1 thioredoxin-ELP:antibody ratio (and hence nearly complete antibody capture)

Capture of the FITC-labeled antibody by the thioredoxin-ELP fusion was demonstrated in two control experiments, one with no specific capture (FIG. 2a) and one with nearly complete capture (FIG. 2b). These experiments also allowed the characterization of baseline fluorescence for both the supernatant and pellet fractions.

In FIG. 2a, the reaction was set up as described in Methods, except that both the unlabeled antibody and thioredoxin-ELP were omitted from the reaction mixture. Because no thioredoxin-ELP was present to capture the FITC-labeled antibody, the precipitate formed after raising the temperature above the $T_t$ contained only free ELP. Therefore, the majority of the fluorescence remained in the supernatant, with only 3.4% of the total fluorescence observed in the pellet. This small amount of residual fluorescence, which represents the background fluorescence for the pellet fraction of the immunoassay, is likely due to incomplete removal of the supernatant and to non-specific trapping of the labeled antibody in the aggregated ELP phase.

In FIG. 2b, a ten-fold greater concentration of thioredoxin-ELP fusion (5 $\mu$M versus 0.5 $\mu$M for the standard assay described in Methods) was added and the unlabeled antibody was omitted. An equilibrium model of binding predicts that 96% of the labeled antibody should be bound at this thioredoxin concentration, assuming a $K_D$ of 1×10$^7$ M (independently determined by BIAcore analysis). However, the fraction of total fluorescence observed in the pellet is 48.4% (when corrected for pellet background fluorescence). We believe that the residual background fluorescence in the supernatant is from contaminating mouse IgG antibodies, which are present in mouse ascites fluid from which the anti-thioredoxin monoclonal antibodies are Protein-A affinity purified. This is supported by previous experiments in which residual antibodies, which remained in the supernatant after one round of capture using thioredoxin-ELP concentrations theoretically sufficient for complete capture, were not captured in a subsequent experiment by a large molar excess of thioredoxin-ELP fusion protein. This result indicates that these residual antibodies do not bind thioredoxin. Hence, if the pelleted fraction contains 96% of the anti-thioredoxin antibodies, then the fraction of contaminating antibodies which do not bind thioredoxin is 49.5%, which represents the background fluorescence for the supernatant fraction of the immunoassay.

Figure 3:
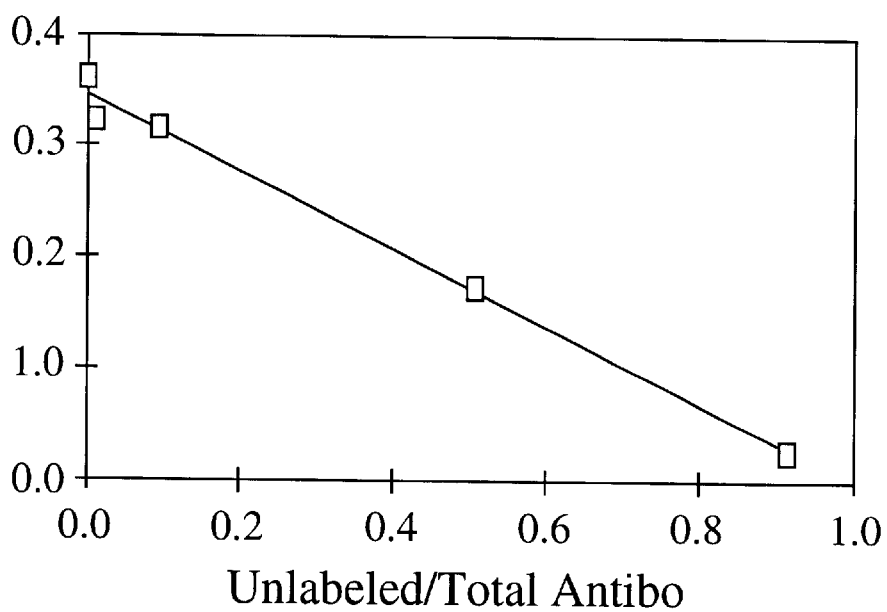
FIG. 3 illustrates an immunoassay calibration curve. The X-axis is the ratio of unlabeled to total antibody concentrations, with points corresponding to unlabeled antibody concentrations of 0, 0.005, 0.05, 0.5, and 5 $\mu$M (left to right). The Y-axis is the ratio of fluorescence in the pellet to total fluorescence (pellet+supernatant), and represents the fraction of labeled anti-thioredoxin antibodies specifically captured.

A calibration curve for the immunoassay is shown in FIG. 3. On the X-axis, the analyte concentration is represented by the ratio of analyte concentration (unlabeled antibody) to total antibody concentration. Data points are in decade increments of absolute analyte concentrations, ranging from 0.005 to 5 $\mu$M. On the Y-axis, the assay output signal is the ratio of the fluorescence intensity of the pellet fraction to the total fluorescence intensity (i.e., the summed fluorescence intensities of the pellet and the supernatant). The background fluorescence was subtracted from the intensities for both the supernatant and pellet. Because the fluorescence intensity is quantitatively related to the concentration of the labeled anti-thioredoxin antibody, this ratio is the fraction of labeled antibody that binds to the thioredoxin-ELP fusion and is precipitated.

Qualitatively, the curve indicates that as the fraction of unlabeled antibody increases, the fraction of labeled antibody bound decreases, as expected for a competitive binding assay. Conversely, as the fraction of unlabeled antibody decreases, the fraction of labeled antibody bound increases, approaching a maximum where no competing unlabeled antibody is bound. The data exhibits a near linear relationship ($R^2$=0.993). However the shape of the curve could be non-linear under other immunoassay conditions, as described below. Once generated, the calibration curve can then be used to quantitatively determine the concentration of unlabeled antibody in unknown samples.

Two primary parameters by which any immunoassay is judged are sensitivity and dynamic range. This competitive capture assay has a maximum sensitivity when the concentration of unlabeled analyte is equal to that of the competing labeled antibody (i.e., 0.5 on the X-axis in FIG. 3). As the concentration of unlabeled analyte is decreased or increased from this point (e.g., moving on the calibration curve left or right from center), the interval for each successive decade in absolute concentration of analyte decreases, thereby reducing signal sensitivity. In this particular case, the immunoassay's maximum sensitivity was focused on an analyte concentration of 0.5 $\mu$M, determined by the selection of that same concentration for the FITC-labeled antibody. This center of sensitivity could be shifted, or focused, by simply varying the labeled antibody concentration. The range over which this shift could be achieved would be limited in higher concentrations only by the supply of reagents and in lower concentrations by the antibody's binding affinity. The antibody affinity, and hence the lower limit for this particular assay, are as yet undetermined. However, preliminary calculations indicate that the antibody affinity is on the order 0.1 $\mu$M, yielding a lower limit for the center of sensitivity of approximately the same magnitude. It is worth noting that this affinity is relatively low when compared to many antibodies, and therefore significantly lower concentrations could be measured with immunoassays utilizing higher affinity binding pairs.

The dynamic range of a particular immunoassay (that is, the useful range on either side of a given center of sensitivity) is determined primarily by the sensitivity of the fluorimeter or other reporter detection instrumentation. For the data in FIG. 3, the range for the most highly sensitive concentration measurements spans roughly two orders of magnitude (ranging from 50 nM to 5 µM). At least two additional orders of magnitude (one on each end of this range) could be determined with a sensitivity roughly 10% of that for the central region, for a total range of 5 nM to 50 µM. The absolute upper and lower limits of the useful range about the center of sensitivity have not yet been determined experimentally, but may even exceed this preliminary estimate of four orders of magnitude.

Just as the selection of the labeled antibody concentration has important ramifications on the center of sensitivity, equilibrium models of competitive binding reveal that the selection of antigen (thioredoxin-ELP) concentration critically affects the shape of the calibration curve, as alluded to earlier. Specifically, if the antigen concentration is higher than the labeled antibody concentration, then the curve takes on a non-linear shape with a plateau at lower unlabeled antibody concentrations giving way to a rapid drop-off in signal at higher antibody concentrations. This results in a significant decrease in the dynamic range of the assay. On the other hand, as the antigen concentration becomes smaller than the labeled antibody concentration, the curve takes on a more linear shape which is also accompanied by an overall reduction in fraction of total antibody bound and captured, and hence a reduction in signal sensitivity. The optimum conditions for the assay, therefore, requires equal concentrations of antigen and labeled antibody, which produces both a nearly linear curve and maximum sensitivity. However, this parameter could be varied depending on the requirements of a particular immunoassay, with high antigen concentrations used to achieve very high sensitivity over a small dynamic range, or conversely low antigen concentrations used to achieve a very broad range with reduced overall sensitivity.

The precipitation of the ELP-antibody-antigen complex can be induced by increasing the solution temperature above the $T_t$, as was done in the example immunoassay presented here, or by increasing the ionic strength of the solution, or a combination of both. The $T_t$ of a given ELP construct is decreased as the ionic strength of the solution is increased. Therefore, aggregation may be induced isothermally by increasing the ionic strength such that the ELP $T_t$ is depressed below the solution temperature. In addition, the ELP phase transition can also be induced in modified ELP sequences containing appropriate residues by known changes in pH, or in response to chemical or biochemical modification (e.g., phosphorylation). Our claim for this immunoassay therefore covers any physical, chemical, or biological phenomenon that can induce a phase transition in an ELP sequence or its derivatives.

Selection of the means of precipitation depends primarily on ease of use, equipment available, and avoidance of potential deleterious effects on the reactants. For example, high saline concentrations could interfere with antibody binding, while high temperatures could cause protein denaturing. However, sufficient flexibility exists in the design of the ELP $T_t$ that gentle conditions for precipitation should be obtainable for any prospective application.

The ELP-precipitation immunoassay method presented here could be used in a number of different configurations or formats known to those skilled in the art. Flexibility in this assay arises from the following factors, which can be implemented in any combination: either one of the binding partners can be attached to the ELP, either one of the binding partners can be reporter-labeled, and either one of the binding partners can be the analyte. Flexibility can be further expanded by the use of a secondary antibody ("Indirect assay") or an antibody with a non-overlapping epitope ("Sandwich"). These configurations simplify the initial immunoassay reaction and eliminate the need for labeling of the reagent (which may otherwise reduce affinity), but require a secondary incubation and precipitation step.

The only limitation in these configurations is that the antibody cannot be both fused to an ELP and labeled with a reporter because, in this configuration, no reporter could ever be captured. Another requirement for all configurations is that for quantitative detection, only the analyte (and not its affinity partner) can occur in the unknown sample.

Selection of a particular configuration would depend primarily upon the availability of a gene for one of the binding partners. The availability of sufficient quantities of reagent as the labeled species may also be an important consideration. One of the species may not be at all available as a reagent. In this case, configurations exist for which the analyte can be previously unknown. This could be useful, for example, in screening libraries of engineered antibodies for molecules specific to a particular antigen.

This immunoassay is also amenable to the measurement of multiple analytes in a single sample using a set of analyte-binding proteins, each of which is specific to an analyte of interest. Detection of each analyte can be achieved by two alternative strategies. In the first approach, each analyte-binding protein is attached to a distinct reporter (e.g., fluorophores with unique excitation and emission properties). The assay would be performed identically to that for a single analyte, and independent detection of each analyte would be simultaneously achieved by monitoring the unique spectroscopic signal for each reporter.

The alternative approach, a sequential detection scheme, would utilize fusion of each antigen or antibody to ELPs with different $T_t$'s. The non-covalent complexes formed would be sequentially and independently precipitated, thereby allowing separate measurement of each analyte. This approach requires ELPs with distinct, non-overlapping $T_t$'s, which can be achieved by a combination of varying the identity of the guest residue and by varying the ELP molecular weight. We have previously demonstrated the feasibility of this approach by the synthesis of ELPs of varying chain length exhibiting different $T_t$'s, and we can further expand upon the available range of $T_t$'s available by producing ELPs with different compositions.

The genetic attachment of the ELP provides several key advantages as compared to chemically-conjugated, synthetic temperature-sensitive polymers outlined in patent WO 86/06492. First, this method of synthesizing the thermally precipitating reagent is technically simpler and less costly, with no need for separate and often complex synthesis of the polymer nor for a subsequent chemical conjugation step to couple the immunoassay reactant to the thermally-responsive polymer. Second, the genetically-produced ELP is monodisperse, whereas production of synthetic polymers results in a population of molecules with varying chain lengths. This heterogeneity may adversely affect the performance of the immunoassay by, for example, shifting or broadening the range of temperatures over which the phase transition occurs. Finally, genetic fusion allows absolute control over the number (typically one) and location of the ELP(s) in the fusion protein. Chemical conjugation of a synthetic polymer to a protein, in contrast, usually results in random attachment of the polymer at conjugation sites located throughout the primary amino acid sequence of the protein, resulting in varied numbers and diverse locations of attached polymers. If any of these conjugation sites are near the binding site, reduction of affinity or complete blockage of binding results, thereby adversely affecting the performance of the immunoassay. Furthermore, chemical conjugation of protein and polymer is inefficient and incomplete, whereas genetic ELP incorporation insures that every molecule has exactly the same structure and properties.

In summary, the immunoassay described herein provides a novel method for reactions in which at least one of the binding partners is a recombinant protein. It has important advantages over similar methods in terms of simplicity and precision of reagent production. It is flexible and can be utilized in a variety of configurations, and can be readily automated. Finally, it provides high sensitivity over a wide range of medically-relevant analyte concentrations.

EXAMPLE 3

Sensor Regeneration with a Thioredoxin-ELP Fusion Protein

This examples shows that an environmentally-responsive polypeptide tag can be introduced into a model protein by genetic engineering, that the polypeptide tag allows the fusion protein to adsorb to a hydrophobic surface, and that the fusion protein can be desorbed from the surface by altering the solvation of the protein in response to an environmental signal, thereby allowing regeneration of the surface back to the protein-free substrate. This approach is generic for the following reasons: first, the introduction of enviromentally-triggered properties in a target protein simply involves gene-level N or-C-terminal fusion of the peptide codons into a cloned or synthetic gene, which is easily achieved by standard molecular biology manipulations. Second, fusion proteins containing this polypeptide tag are rendered environmentally-responsive, and this appears to be a fairly general phenomena. Finally, the polypeptide tag can be chemically conjugated to molecules that are not genetically-encodable, thereby creating an environmentally-responsive bioconjugate that can be reversibly adsorbed and desorbed by small changes in solution conditions.

A. Experimental Details

Solution Inverse Transition. The optical absorbance at 350 nm of the thioredoxin-ELP fusion protein was monitored in the 4–60° C. range on a Cary Bio-300 UV-visible spectrophotometer, equipped with a multi-cell peltier temperature controller. The $T_t$ was determined from the midpoint of the change in optical absorbance at 350 nm due to aggregation of ELP or thioredoxin-ELP fusion protein as a function of temperature at a heating or cooling rate of 1–1.5° C. min$^{-1}$.

Substrate Preparation: Gold substrate were prepared by thermal evaporation of 50 Å Cr on a silicon wafer (for ellipsometry) or glass slide (for BIACORE instrument measurements) followed by 500 Å gold. The gold substrate were cleaned in a 1:1:3 solution of $NH_4OH:H_2O_2:H_2O$ and incubated overnight in a 1 mM solution of hexadecanethiol in ethanol to form a self-assembled monolayer (SAM) on gold. The SAMs were sonicated in ethanol for 1 min, dried under nitrogen and used immediately thereafter. Advancing water contact angle of the SAMs were ~100°. for the hydrophobic SAM of hexadecanethiol.

In situ Ellipsometry. The SAMs were mounted on the ellipsometer stage in a cuvet and the cuvet was filled with 50 mM phosphate, pH 7.4, 1 M NaCl. The polarizer and analyzer angle of the thiol-functionalized gold substrate were measured in buffer and converted to ellipsometric parameters ($\psi$, $\Delta$). Next, a concentrated stock solution of thioredoxin/ELP fusion protein was pipetted into the cuvet to a final concentration of 1 $\mu$M. The time course of adsorption of the fusion protein on SAM-functionalized gold substrates was examined by in situ ellipsometry as the ELP underwent a hydrophilic-hydrophobic transition as the temperature was raised from 15–40° C. at ~1° C. min$^{-1}$. The ellipsometer cuvet was heated and cooled by an immersion coil connected to a thermally programmable (−20–100° C.) recirculating water bath. The in situ temperature of the buffer in the cuvet was measured by a thermocouple at each time point for which ellipsometric parameters were measured. The polarizer and analyzer angles were monitored through the thermal ramp on the upward and downward cycle and were used in a nonlinear regression simulation program to obtain thickness and complex refractive indices for the silicon substrate, silicon oxide, gold, SAM, and protein overlayers. Effective thickness of the protein adlayer was calculated assuming a protein refractive index of 1.45.

BIACORE™ Instrument Analysis: Typically, a gold-coated glass slide was mounted in an empty BIACORE™ sensor cartridge using water-insoluble double-sided sticky tape. The sensor cartridge was docked into a BIACORE X™ instrument system, and a system check was performed to ensure the absence of leaks in the fluid path and minimal baseline drift. The cartridge was then removed from the instrument and cooled to low temperature (approximately −20° C.). The sensor surface was incubated with 1 $\mu$M thioredoxin-ELP fusion protein in 2 M NaCl at ~4° C., warmed to room temperature to allow the fusion protein to undergo the phase transition, and adsorbed to the sensor surface for 5 min. Excess protein was washed away with buffered 2M NaCl at room temperature and the sensor cartridge was then reinserted into the BIACORE X™ instrument, which was maintained at 35° C. All buffers used for BIACORE™ instrument measurements were 50 mM potassium phosphate, pH 7.4 of varying NaCl concentrations.

B. Results and Discussion

Design of ELP Carrier. Based on previous studies that have delineated the effect of varying the identity of the fourth, guest residue (X) in the repeat unit, and its mole fraction on the $T_t$, a gene was synthesized encoding an ELP sequence with guest residues Val (V), Ala (A), and Gly (G) in the ratio 5:2:3 in accordance with the procedures described in Example 1 above to provide a solution $T_t$ in water of ~37° C. By adjusting the sequence length, as well as its composition, we can design sequences that undergo the inverse transition at any temperature between 0 and 100° C. The ELP-1 mer (50 amino acids) was oligomerized to produce a library of ELP oligomers at the gene level. The 18-mer was chosen as a carrier polypeptide in the first generation expression vector, based on its experimentally-observed $T_t$.

Figure 4:
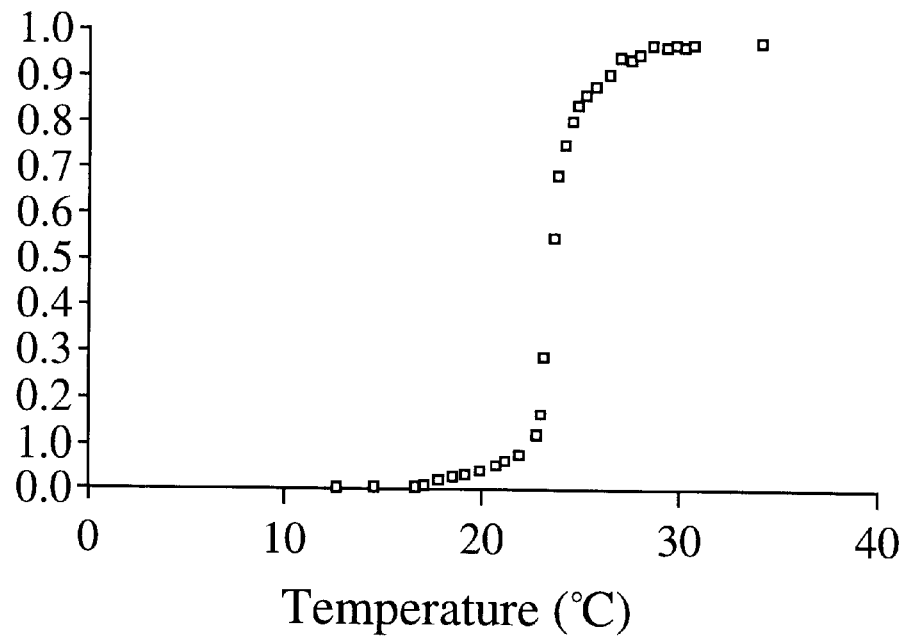
FIG. 4. Absorbance at 350 nm of the thioredoxin-ELP 18-mer by UV-visible spectrophotometry in 50 mM phosphate, pH 7.4, 1 M NaCl. Relative turbidity is defined as the absorbance at 350 nm (due to scattering) normalized to the maximum absorbance at the same wavelength during the course of the experiment.

Inverse Transition of Thioredoxin-ELP Fusion Protein in Solution. The inverse transition of thioredoxin-ELP 1 8-mer fusion protein (25 $\mu$M fusion protein in 50 mM phosphate, 1 M NaCl) as a function of temperature (1.5° C. min$^{-1}$ heating rate) is shown in FIG. 4. With the exception of a higher concentration of fusion protein, these experimental conditions are identical to those used for surface regeneration. As the temperature was raised, the turbidity of the solution, spectrophotometrically monitored by the absorbance at 350 nm, stayed constant up to a certain temperature. Further increase in temperature resulted in a sharp (<2° C.) increase in the turbidity to a maximum value, due to aggregation of the thioredoxin-ELP fusion protein. The inverse transition temperature ($T_t$) is defined as the midpoint of the spectrophotometrically observed transition. The experimentally-observed $T_t$ of the thioredoxin-ELP fusion was 25° C., which was identical to that of the ELP with no fusion partner (results for ELP not shown), demonstrating that the inverse transition of the ELP was not affected by conjugation to thioredoxin. This process was reversible with slight hysteresis, and the aggregated fusion protein could be resolubilized completely by lowering the temperature below the $T_t$. The thioredoxin control exhibited no change in absorbance with increasing temperature. We also observed complete retention of thioredoxin activity after several rounds of thermal cycling. These results validate our first hypothesis, that the inverse transition of the ELP sequence is retained upon its expression in a fusion protein, and that the ELP tag does not compromise the activity of the target protein, which is critical for biosensor applications.

Surface Binding and Regeneration of Thioredoxin-ELP Fusion Protein. This experiment was designed to investigate the hypothesis that desolvation of the ELP sequence upon raising the temperature above its $T_t$ will drive a protein to the surface via hydrophobic interactions between the desolvated, hydrophobic ELP sequence and the hydrophobic surface. Subsequently, upon lowering the temperature below the $T_t$, the ELP sequence solvates and becomes hydrophilic, which should lead to spontaneous desorption of the ELP fusion protein from the surface.

Figure 5:
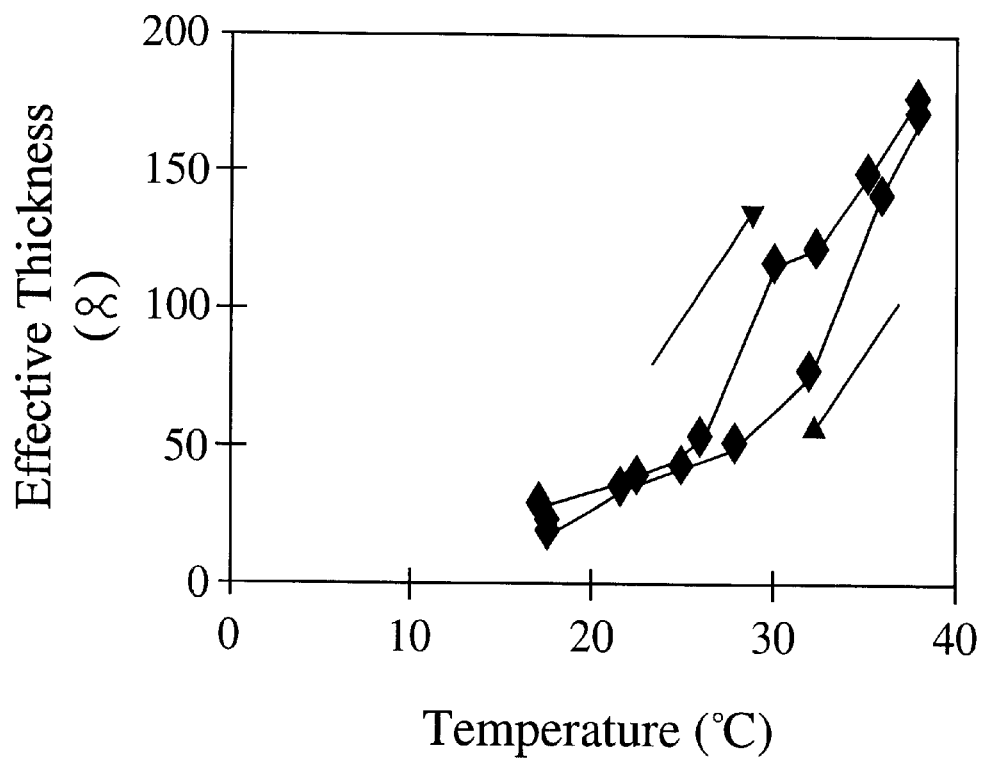
FIG. 5. In situ ellipsometry measurements of the change in adlayer thickness of the thioredoxin-ELP fusion protein in contact with a hydrophobic SAM as a function of temperature, calculated by nonlinear regression using the measured values of the polarizer and analyzer angles. The thickness of the protein adlayer measured by ellipsometry increases as the temperature is raised through the $T_t$ to a maximum of 180 Å, and decreases to within 5 Å of the baseline thickness upon lowering the temperature to ~18° C.

The adsorption of the fusion protein on the hydrophobic SAM was examined by in situ ellipsometry as the ELP underwent a hydrophilic-hydrophobic transition in 50 mM phosphate, 1 M NaCl as the temperature was raised from 15 –40° C. at a rate of 1° C. $\min^{-1}$. The polarizer and analyzer angles were monitored through the temperature ramp. FIG. 5 shows the change in thickness of the protein adlayer as a function of temperature, calculated by nonlinear regression using the measured values of the polarizer and analyzer angles. The increase in adlayer thickness with increasing temperature clearly shows that as the thioredoxin-ELP fusion protein undergoes its inverse transition, it adsorbs to the hydrophobic SAM during the upward thermal ramp. The observed inverse transition of the ELP on the hydrophobic surface is broader than the equivalent bulk transition. The ELP forms a stable adlayer on the hydrophobic surface above the transition temperature. Upon lowering the temperature to ~20° C., the adsorbed thioredoxin-ELP fusion protein desorbs from the surface. Desorption is essentially complete as seen by the <5 Å change in surface thickness after one thermal cycle.

In separate experiments, we have established that the adsorbed protein completely desorbs from the surface, if the maximum temperature in the cuvet is kept below 40° C. This process can be repeated several times with virtually no irreversibility. A control experiment with thioredoxin alone, showed little adsorption of thioredoxin in the time scale of the experiment, and all of it was irreversible. This experiment demonstrates the reversible adsorption/desorption of an ELP fusion protein in response to a thermal stimulus.

Analyte Binding and Surface Regeneration by Surface Plasmon Resonance. The objective of this set of experiments was to demonstrate that adsorbed thioredoxin-ELP fusion protein can bind to an analyte, anti-thioredoxin mAb, and that the antibody-fusion protein complex can be desorbed after binding. This objective can be achieved if the following can be demonstrated:

1) Thioredoxin is exposed to the bulk after immobilization of the ELP-thioredoxin fusion protein.

2) A monoclonal antibody against thioredoxin can bind to the surface-immobilized thioredoxin.

3) The thioredoxin-ELP/antibody complex remains immobilized above the phase transition over time.

4) Thioredoxin-ELP/antibody complex can be desorbed from the surface upon lowering the temperature below the phase transition temperature.

The BIACORE™ device divides the sensor surface into two channels which can be addressed individually. This allows use of one channel as a reference, and all signals presented here are difference signals between channel 1 (measurement) and channel 2 (reference). As shown in FIG. 6, the bare surface [A] has a signal difference between channel 1 and channel 2 of about 530 Response Units (RU). This is due to small variations in substrate preparation. At time [1] the sensor surface, to which the thioredoxin-ELP fusion protein is adsorbed above the $T_t$ outside the instrument is inserted [B] and a slight increase in signal difference to about 725 RU is found, which may be due to the insertion process. The reference channel 2 is then rinsed with pure water for 5 minutes [2] which removes the adsorbed thioredoxin-ELP fusion protein from the sensor surface in this channel. The signal difference [C] of about 3300 RU corresponds to the amount of adsorbed thioredoxin-ELP fusion protein in channel 1. At high salt concentration, 2 M NaCl in the running buffer, the signal is stable, but antibody binding is inefficient. Therefore the salt concentration in the running buffer was reduced to 1 M NaCl [3], which leads to a slow desorption [D] of about 20% of the protein in about 1000 sec. The stable desorption rate is about 0.4 RU/sec.

Anti-thioredoxin binding. Channel 1 is selectively incubated with 50 µl anti-thioredoxin mAb (1:10 dilution) in running buffer [4]. The signal increases by about 1600 RU [E] indicating strong antibody binding. Upon completion of binding, only the time-dependent desorption at a rate of 0.4 RU/sec is observed.

Figure 7:
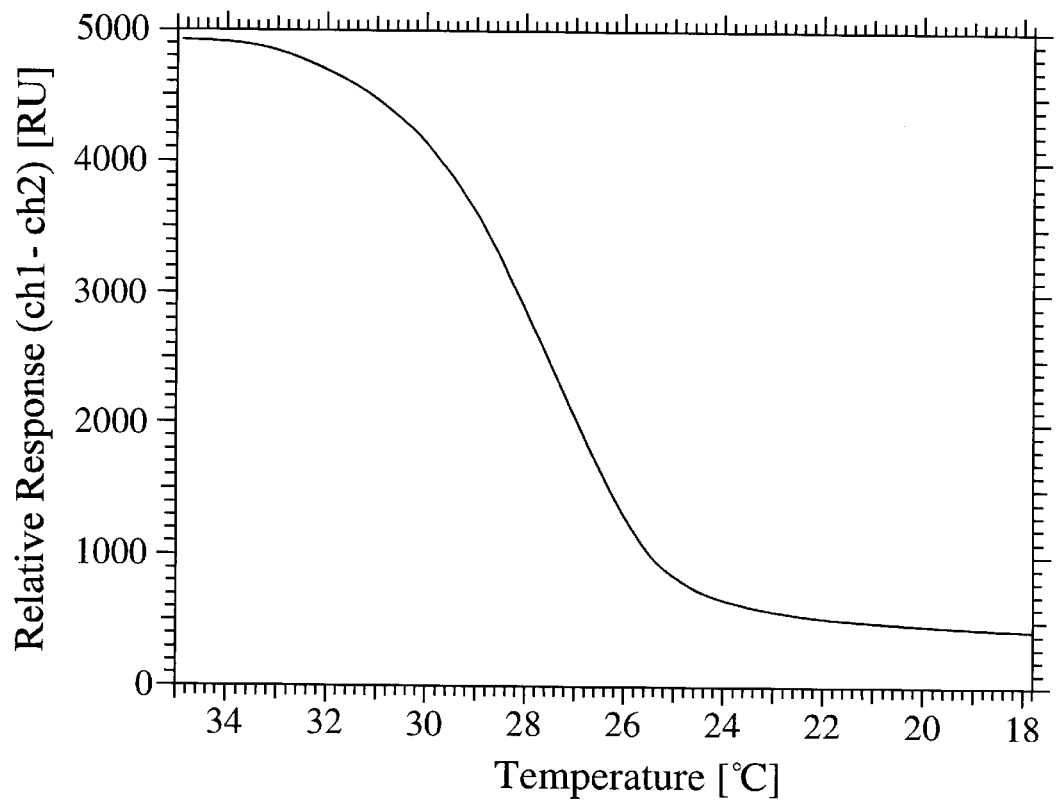
FIG. 7 illustrates desorption of thioredoxin-ELP fusion protein monitored by the SPR signal relative to control channel as a function of temperature.

Desorption. The sensor temperature can be changed in the BiacoreX, and although the temperature change is not linear with time, the temperature is measured at the sensor surface, and can be monitored as a function of time. Upon lowering the temperature [5] from 35° C. to 18° C. the signal decreases [F] to approximately the same level (400 RU) as the bare sensor surface. FIG. 7 shows the desorption process as a function of temperature.

These experiments demonstrate that a thioredoxin-ELP fusion protein adsorbs to a hydrophobic surface and can be desorbed completely by a small change of environmental conditions. The observation that after adsorption of the fusion protein, thioredoxin binds to an anti-thioredoxin mAb, suggests that the water soluble thioredoxin exposed to the bulk and accessible to its antibody. The immobilized complex is stable at the surface; in a separate experiment with a running buffer containing 2 M NaCl, after mAb binding, the SPR was stable to within 0.08 RU/sec over several hours, though the affinity for antibody binding is reduced at these salt concentrations (data not shown). Together, these independent experiments show that the noncovalent complex of fusion protein and antibody can be immobilized on the surface with high stability. Finally, the complex can be desorbed completely from the surface by lowering the temperature below the phase transition temperature (aim 4).

These data indicate the feasibility of creating a regenerable surface with the desired sensing specificity in accordance with the present invention. We believe that our approach to sensor regeneration is powerful and generic. This is because an analyte-binding protein for biosensor applications can easily be produced as a fusion with an ELP tag using standard molecular biology methods with no loss of functional activity. For other molecules which cannot be produced as a genetically-encoded fusion with an ELP, including proteins for which a cloned or synthetic gene is unavailable, the ELP tag can be chemically or biochemically-conjugated to the target molecule. Creating a reversible biosensor surface then only requires a hydrophobic surface, which is also easily achieved by a variety of surface functionalization methods, including SAMs on gold, silane modification of glass or oxidized silicon, or any other method that provides a hydrophobic surface. Combined, the environmentally-triggered, reversible interaction of an ELP fusion protein and a hydrophobic surface allows facile regeneration of biosensors.

EXAMPLE 4

Targeted Delivery of Therapeutics to Solid Tumors By Thermally Responsive Polymers Because targeting is necessary for efficient tumor localization of systemically-delivered therapeutics, we propose a thermal targeting scheme, where a thermally-responsive drug carrier precipitates in regions of elevated temperature.

Polymers that undergo an inverse temperature transition are useful as drug carriers for thermal targeting because they are soluble in aqueous solutions below their inverse transition temperature ($T_t$), but when the temperature is raised above their $T_t$, they undergo a narrow phase transition within a 2–3° C. range, leading to extensive desolvation and aggregation. Elastin-like protein (ELP) biopolymers [D. Urry, *J. Prot. Chem.* 7: 1–34 (1988); D. Urry, *Prog. Biophys. Molec. Biol.* 57: 23–57 (1992)] and copolymers of poly(N-isopropylacrylamide) (poly(NIPAAm)) [H. Schihld; *Protg. Polym. Sci.* 17: 163–249 (1992); C. Chiklis and J. Grasshof, *J. Polym. Sci. Part A-2* 8: 1617 (1970); L. Taylor and L. Cerankowski, *J. Polym. Sci. Polym. Chem.* 13: 2551 (1975); Y. Takei, *Bioconj. Chem.* 4: 42 (1993)] are two polymer systems that can be designed to display this behavior slightly above physiological temperature. ELP biopolymers can be designed to exhibit a $T_t$ within a <2° C. range between 0–100° C. by specifying the identity and fraction of the fourth residue [D. Urry et al., *J. Am. Chem. Soc.* 113: 4346 (1991)]. Chemically synthesized copolymers of NIPAAm and alkylacrylamides, display a similar phase transition, the midpoint of which can similarly be tuned by varying the fraction of the NIPAAm monomer. To date, neither of these polymers have been utilized as radionuclide carriers for targeted drug delivery by hyperthermia.

A. Methods

Gene synthesis, oligomerization, protein expression, purification, Poly (NIPAAm) synthesis and inverse transition temperature characterization are described in Example 1 above.

Conjugation of Fluorophore. Approximately 11 milligrams of thrombin-cleaved ELP-15 mer or the poly (NIPAAm/AAm) copolymer were resuspended in 1 ml 100 mM sodium bicarbonate buffer, pH 8.34. 40 µl of Rhodamine Red-X™ succinimidyl ester (10 mg/ml in DMF) was added and incubated with gentle agitation for 2 hours at room temperature. After incubation, the sample was centrifuged at 10,000 g for 5 min. to remove insoluble matter. The supernatant was then thermally purified by adding NaCl to 500 mM, heating to 35° C., and centrifugation at T≧35° C. at 10,000 g for 5 minutes. The supernatant was removed, the pellet was resuspended in cold PBS, and centrifuged cold. The resolubilized conjugate was retained. The thermal purification was repeated twice. Conjugation efficiency for the ELP 15-mer was determined by BCA total protein assay and by rhodamine absorption at 570 nm.

Tumor Vascular Preparation. A small volume (~0.1 mm³) of tumor tissue (human ovarian carcinoma; SKOV-3) was implanted in the dorsal skin flap window chamber in nude mice. The implanted tumors were used 10–15 days after surgery, when the tumor in the window chamber was 2–3 mm in diameter. The implanted tumors in the window chamber can be placed under a microscope so that the injected material of interest can be directly visualized in the vascular and interstitial compartments and its concentration can be directly measured.

Experimental Procedure for Mouse Window Chamber Technique. In each experiment, a mouse was anesthetized with sodium pentobarbital. The tail vein was cannulated to allow injection of the Rhodamine-ELP conjugate. After cannulation, the animal was placed on a temperature-controlled microscope stage to maintain normal body temperature throughout the experiment. The tumor in the window chamber was observed with a 20× objective. A region of the preparation was selected such that blood flow appeared to be normal and did not have any other blood vessels below it. Images of the selected region were recorded by a SIT camera connected to a S-VHS recorder under epifluorescent illumination before injection of the ELP-Rhodamine conjugate. After injection of the conjugate (t=0), the image from the selected region was recorded every 2 min. for 5 sec over a duration of 40 min. The videotape was analyzed by image processing software (NIH Image) on an IBM-compatible-PC. At any time, the light intensity of the entire tissue area $I_t$, and a representative vascular region ($I_v$) and interstitial region ($I_i$) were analyzed to provide the time dependence of $I_v$ and $I_i$.

B. Results

Design, Synthesis, Purification, and Characterization of ELP Biopolymer and Poly(NIPAAm/AAm) Copolymer. The transition temperature of an ELP biopolymer is strongly influenced by the hydrophobicity of the guest residue (X) and its mole fraction $f_x$. Therefore, by varying the identity of guest residues, and their mole fraction, ELP copolymers can be designed to exhibit a predetermined inverse transition temperature in a 0–100° C. range. Based on these previous studies, a synthetic gene for the monomer, which encodes 10 VPGXG repeats, was designed to incorporate guest residues: X=valine (V), alanine (A), and glycine (G) in the ratio 5:2:3 to achieve a $T_t$ of 42° C. Standard molecular biology procedures were used to construct the synthetic gene of the ELP monomer, and to oligomerize the gene to create a library ranging from 1 to 18-mer where each monomer contains 50 residues.

In initial studies, the ELP 6-, 9-, 12- and 18-mers were expressed in *E. coli* in a modified pET-32b expression vector as a fusion with thioredoxin. Each fusion protein retained the reversible phase transition of the ELP sequence, which allowed one-step thermal purification of the thioredoxin-ELP fusion from all other soluble *E. coli* contaminants. The amino acid sequence of the fusion protein has a recognition site specific to thrombin, located between thioredoxin and the ELP sequence. Cleavage with thrombin at this site liberated the ELP from the fusion protein. Thermal precipitation of the ELP was then used to purify the ELP from other proteins. Because the thermally-induced aggregation of ELP biopolymer is completely reversible in vitro, the ELP was then solubilized for subsequent experiments by simply lowering the temperature below its $T_t$. The observation that the thioredoxin fusion protein containing a C-terminal ELP sequence also exhibits an inverse transition indistinguishable from the ELP sequence alone is exciting, because it indicates that thermal targeting will also be applicable to the delivery of protein therapeutics to tumors.

Figure 8:
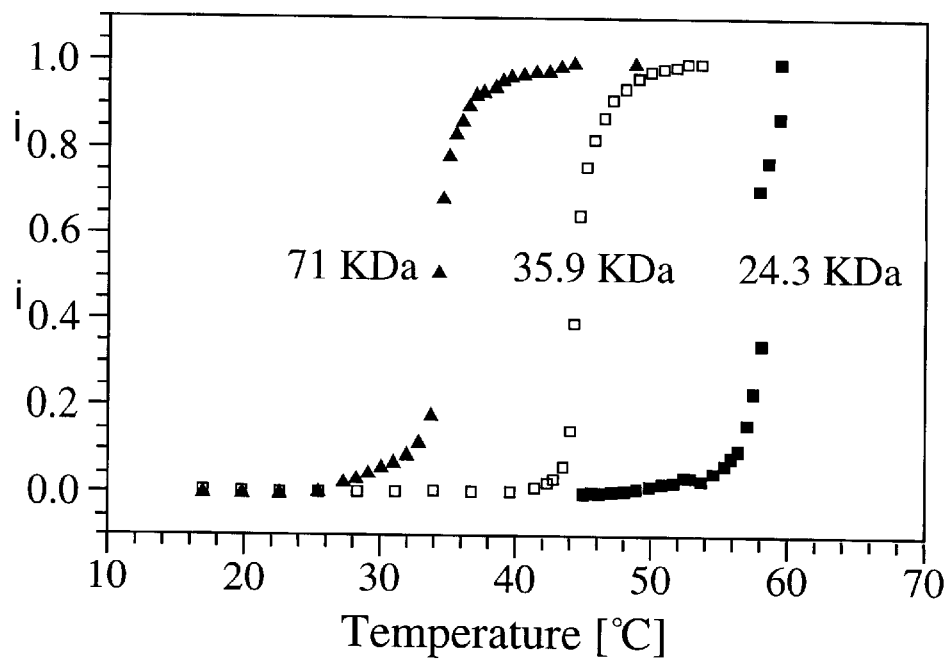
FIG. 8. Absorbance at 350 nm of the ELP 6-mer (filled squares). 9-mer (open squares), and 18-mer (filled triangles) as a function of temperature.

The thermal behavior of the ELP 6, 9, and 18-mer (MWs=24.3 kDa, 35.9 kDa, and 71 kDa, respectively) in PBS ranged from 58.7° C. to 35.1° C. is shown in FIG. 8, and reveals a strong inverse relation between MW and $T_t$, which is consistent with previous observations of Urry and colleagues for ELPs with MWs <100 kDa. Interpolation of these results suggested that an ELP 15-mer (MW ~50 KDa) would allow the target $T_t$ of 40–42° C. to be achieved with the current ELP composition, containing guest residues Val:Ala:Gly in a 5:2:3 ratio.

Figure 9:
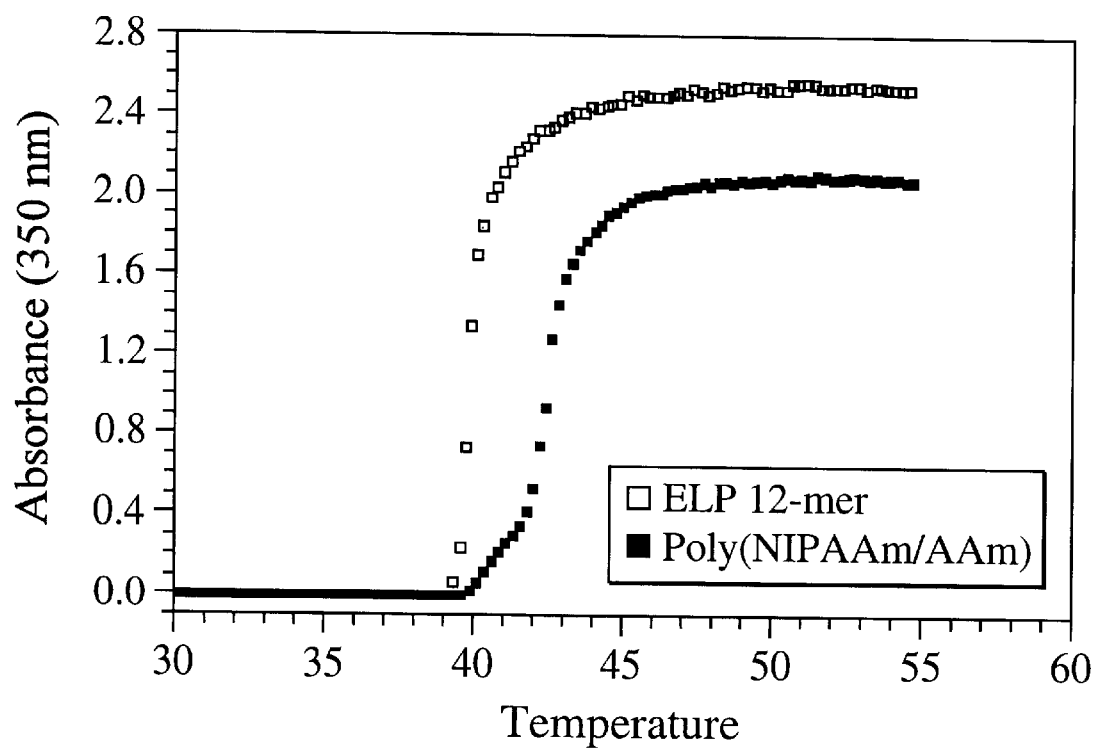
FIG. 9. Absorbance at 350 nm of the ELP 15-mer (filled squares) and poly(NIPAAm/AAm) copolymer (open squares) by UV-visible spectrophotometry.

The ELP 15-mer was then synthesized and purified in mg quantities. FIG. 9 displays the thermal behavior of the ELP 12-mer in physiological saline. The $T_t$ of the ELP 15-mer, defined as the midpoint of the experimentally-observed inverse transition, is 42.5° C. The inverse transition of this polymer occurs over a narrow, <3° C. range, which is important for hyperthermic targeting. While the first generation ELP 5-mer construct will be useful for in vivo radionuclide delivery, it would be desirable to have in hand additional constructs with MWs in the 10–30 kDa range with a $T_t$ of 40° C., in order to explore the relationship between ELP MW and radionuclide biodistribution. Based on previous studies by Urry et al., the Val:Ala:Gly ratio is decreased to 5:1:1 to yield a polymer of 25 kDa MW and a $T_t$ of 40° C. and is useful in the same manner as described above.

The thermal behavior of the poly(NIPAAm/AAm) copolymer is also shown in FIG. 9, and clearly demonstrates that the inverse transition occurs in a narrow, 2° C. range, and that the $T_t$ is 41° C. The copolymer contains one amine end group per polymer chain for conjugation of amine-reactive radionuclides. Future rounds of synthesis can be carried out to provide a library of copolymers with MWs in the 10–50 kDa range by adjusting the concentration of initiator and chain transfer agent relative to monomer. If required, after synthesis the polymers can be fractionated by size to provide polymers with a specified MW and polydispersity.

Characterization of Rhodamine-Polymer Conjugates. The thermal behavior of the ELP 15-mer and its conjugate with Rhodamine is shown in FIG. 10. The conjugation of Rhodamine to the ELP 15-mer results in a decrease in the $T_t$ from 43° C. to 40° C. This is consistent with the increased hydrophobicity of the conjugate, which should result in a decrease in the observed $T_t$. Similarly, conjugation of Rhodamine to the poly(NIPAAm/AAm) copolymer also results in a decrease in the $T_t$ of the conjugate, but the magnitude (~1° C.) is slightly smaller than that observed for the ELP.

Fluorophore Targeting Study: Dorsal Skin Flap Window Model. Equal amounts of Rhodamine-labeled ELP-12 mer (1.1 mg, 200 μl) or poly(NIPAAm) were injected into nude mice bearing subcutaneous ovarian cancer tumors (SKOV-3) at normothermic and hyperthermic temperature into two animals. In one experiment, the window chamber was maintained at normothermic temperature (34° C.), while in the second experiment, the window chamber containing the implanted s.c tumor was heated to 42° C. Results from these two experiments are shown in FIGS. 11a and 11b. Over a period of 40 min., the fluorescence in the vasculature remains constant and approximately equal at both 34° C. and 42° C. However, a significant difference is observed in the interstitial concentration of the Rhodamine-ELP conjugate. At 42° C., the fluorescence intensity is four-fold higher than at 34° C. These results clearly indicate that the ELP is able to extravasate out of the tumor endothelium and preferentially accumulates in the interstitium at 42° C. as compared to 34° C. FIG. 12 also shows the qualitative difference between the behavior of the ELP conjugate at the two different temperatures. FIG. 12a is a captured image of the tumor under hyperthermic conditions (42° C.), and FIG. 12b is a fluorescence image for the normothermic control (34° C.). At 42° C., fluorescent aggregates are clearly visible in the tumor microvasculature, whereas in the control, normothermic animal, no such aggregates are visible, indicating that the ELP conjugate selectively precipitates in the tumor microvasculature at 42° C. These results are consistent with our in vitro experiments, which demonstrated that the $T_t$ of the Rhodamine-ELP conjugate was 39° C. Similar results were also obtained for a Rhodamine-poly(NIPAAm/AAm) copolymer (results not shown).

C. Conclusions

This example demonstrates that:

(1) Two different classes of polymers have been synthesized that display thermally-responsive behavior in the range of 40–42° C. in physiological saline, a temperature range that is clinically relevant for hyperthermia. The two polymers are (a) an artificial polypeptide, based on a pentapeptide repeat found in elastin, and (b) a poly(NIPAAm/AAm) copolymer. The thermally-responsive behavior is manifested as a solubility-insolubility transition, where the polymer is soluble below the $T_t$, and insoluble above the $T_t$.

(2) In vitro, we have also demonstrated that this transition is reversible, so that the polymers can be cycled between their soluble and insoluble states as a function of temperature.

(3) For the ELP polymers, we have demonstrated that upon fusion of an ELP with another protein the thermally-responsive behavior is retained, and is identical to that observed for the ELP alone. This clearly indicates that protein therapeutics can be synthesized in vivo as fusion protein with an ELP carrier, thereby obviating the need for post-expression chemical conjugation.

(4) Both classes of polymers have been synthesized to contain a specified number of reactive groups so as to allow conjugation of fluorophores, radionuclides, and drugs. We conjugated a fluorophore, Rhodamine, both to the ELP and to the poly(NIPAAm/AAm) copolymer. The fluorophore-polymer conjugate conjugated demonstrated a similar $T_t$ (within 1–3° C.) of the unconjugated polymer. This decrease in the $T_t$ after conjugation was addressed by selecting a polymer with a $T_t$ slightly higher than optimal for hyperthermia, i.e., between 42–45° C., so that upon conjugation, the $T_t$ of the conjugate is then in the range of 40–42° C.

(5) The delivery of the thermally-responsive ELP and poly(NIPAAm/AAm) copolymer was investigated with and without hyperthermia. Aggregation and precipitation of both the ELP and the poly(NIPAAm/AAm) copolymer was clearly observed in the tumor window under hyperthermic conditions. No aggregation was observed in the tumor window of normothermic, control mice. Quantitative analysis of the time course of vascular and interstitial concentration of the thermally-responsive polymers showed that upon application of hyperthermia, the interstitial concentration of the ELP was enhanced by a factor of 250% in a 40 min period of hyperthermia over that observed for the normothermic control. We conclude that enhanced delivery of therapeutics can be achieved by conjugation to thermally-responsive macromolecule carriers in concert with the targeted application of hyperthermia to tumors.

EXAMPLE 5

Thermodynamically Addressable Reversible Adsorption of Elastin Fusion Proteins: A New Method to Dynamically Pattern Proteins on Preformed Surface Templates by Switchable Interactions This example shows that in response to its environmentally triggered hydrophilic-hydrophobic phase transition, the elastin-like polypeptide (ELP) drives the adsorption of a thioredoxin-ELP fusion protein onto a hydrophobic SAM, patterned against a background, hydrophilic SAM. The fusion protein can be subsequently desorbed from the surface by resolution of the ELP tag by reversing the phase transition, thereby allowing regeneration of the surface. We call this method to dynamically pattern proteins, thermodynamically addressable reversible patterning of proteins (TRAP). TRAP also enables patterning of a biomolecule specific to the patterned protein by exploiting molecular recognition of the patterned protein by its biomolecular ligand. We demonstrate that the patterned thioredoxin-ELP fusion protein displays selective binding for its ligand, a monoclonal antibody specific to thioredoxin (anti-thioredoxin), thereby enabling the antibody to be patterned onto the patterned fusion protein. After binding of the antibody to the surface, the bound complex can be desorbed from the surface by reversing the phase transition of the ELP. The ability to reversibly pattern a protein and its noncovalent complex by TRAP will, we believe find application in biomaterials, biosensors, and proteomic arrays.

A. Experimental Section

ELP Gene Synthesis. A gene encoding a 50 amino acid sequence was constructed from chemically synthesized oligonucleotides (Integrated DNA Technologies, Inc.) using standard molecular biology protocols. The 50 amino acid sequence contained 10 repeats of the pentapeptide VPGXG, where the guest residues (V, A, and G in a 5:2:3 molar ratio) were selected to provide in $T_t$ of 40 C in water at a concentration of 40 mg/ml. The gene was oligomerized head-to-tail 18 times by standard molecular biology techniques, to produce an oligomeric ELP gene encoding a 900 residue polypeptide.

B. Synthesis of Thioredoxin/ELP Fusion. The DNA sequence of pET-32b (Novagen, Inc.), an expression plasmid containing a gene for thioredoxin, was modified to include a Sfi I restriction site, which permitted insertion of the ELP gene downstream of the thioredoxin gene. The modified plasmid, containing the gene sequence for the thioredoxin-ELP fusion, was transformed into the E. coli strain BLR(DE3) (Novagen Inc.). Shaker flask cultures of the transformed cells were incubated at 37 C to mid-log phase ($A_{600}$=0.8). Protein expression was then induced with 1 mM isopropyl-β-thiogalactopyranoside, and the cultures were incubated for a further 3 h. Cells were lysed by ultrasonication, and the soluble fusion protein was purified from cell lysate by thermally induced aggregation of the thioredoxin-ELP fusion protein, followed by centrifugation to separate the thioredoxin-ELP fusion protein from contaminating E. coli proteins. The fusion protein was subsequently resolubilized in cold buffer at a temperature below the $T_t$. Protein purity was ascertained by SDS-PAGE, and the concentration of the fusion protein was determined spectrophotometrically by its absorbance at 280 nm (UV-1601, Shimadzu Corp.).

Conjugation of Fluorophores. A mouse IgG monoclonal anti-thioredoxin antibody (gift of David Huston, Baylor College of Medicine) was conjugated to fluoroscein-5-isothiocyanate (FITC) (Molecular Probes, Inc.) using the standard isothiocyanate coupling protocol provided by the supplier. Labeled antibody was then separated from unreacted FITC by gel filtration on a Sephadex G-25 column (Pharmacia, Inc.). The concentration of antibody was determined spectrophotometrically and by a BCA total protein assay (Pierce Chemical Company). The fluorophore to protein ratio in the FITC-labeled antibody was approximately 3.0.

Thioredoxin-ELP was labeled with Alexa™488 as follows: 1 ml of thioredoxin-ELP (1.36 mg/ml) in PBS with 0.1M $NaHCO_3$ was added to a vial containing a ten fold molar excess of Alexa™488 N-hydroxysuccinimide (NHS) ester (Molecular Probes). After incubation for 1 h with stirring at a room temperature, unreacted Alexa488 NHS ester were inactivated by adding hydroxylamine. The conjugated thioredoxin-ELP fusion protein and unreacted protein) was separated from free fluorophore by addition of 1.5 M NaCl to isothermally induce the ELP phase transition. The aggregated fusion protein was separated from free fluorophore by centrifugation, and resolubilized in PBS at room temperature. This process was repeated twice. Final labeling mole ratio of Alexa 488 to ELP was ~2, determined by the absorption at 494 nm for Alexa488 ($\epsilon$=71,000 $M^{-1} \cdot cm^{-1}$) and at 280 nm for ELP-Trx ($\epsilon$=19,870 $M^{-1} \cdot cm^{-1}$).

Solution Characterization of Thioredoxin-ELP Fusion. The optical density of the thioredoxin-ELP fusion protein was monitored at 350 nm as a function of temperature, at a rate of 1 C $min^{-1}$, in an UV-vis spectrophotometer (Varian, Cary Bio-300) equipped with a thermoelectrically controlled multiple cell holder. The temperature-dependent aggregation behavior of the thioredoxin-ELP fusion protein was characterized by its inverse transition temperature ($T_t$), which is defined as the temperature at which the optical density at 350 nm is 5% of the maximum optical density at that wavelength.

Preparation of Patterned SAMs on gold. Thin gold films were prepared by thermal evaporation of 50 Å Cr on a silicon wafer (for ellipsometry) or glass slide (for Biacore measurements) followed by 500 Å gold (Biacore analysis) and 2000 Å (elliposmtery). Thin gold films for SPR analysis (12 mm×12 mm) were also obtained from Biacore Inc. The gold substrate obtained from Biacore Inc. were cleaned in Piranha solution—a mixture of 30% $H_2O_2$ and 70% $H_2SO_4$ (v/v) at 80° C. for 10 min, and subsequently in a 5:1:1 (v/v) mixture of $H_2O$, $H_2O_2$ and $NH_3$ at 80 C for 10 min. The gold substrates prepared in house were cleaned in a 1:1:3 solution of $NH_4OH:H_2O_2:H_2O$.

For solution self assembly of SAMs onto gold, a freshly prepared and cleaned gold film was incubated overnight in a 1 mM solution of hexadecanethiol (HDT, Aldrich) or 11-mercapto-1-undecanol (MUOH, Aldrich) in ethanol. The SAMs were then sonicated in ethanol for 1 min, dried under nitrogen and used immediately thereafter. For μCP, a cotton swab was wetted with a solution of hexadecanethiol (HDT, 1 mM in ethanol, Aldrich Chemical Co.) and dragged once across the face of a plasma-oxidized polydimethylsiloxane (PDMS) stamp. Details of the fabrication of the PDMS stamps with micrometer size relief features have been reported elsewhere (ref). The stamp was dried with a stream of nitrogen for 10 s and placed gently on the cleaned gold substrate. After 2 min, the stamp was removed from the gold substrate. The printed gold substrate was immersed immediately in a solution of MUOH, for 2 min and rinsed with ethanol. The patterned gold substrate was further cleaned with ethanol for 5 min in an ultrasonic water bath and dried in a stream of nitrogen.

Ellipsometry. A manual nulling ellipsometer, built in house, was used for all ellipsometric measurements. A He-Ne laser (632.8 nm, Melles Griot) incident at an angle of 68.25 was used as the light source for intensity as well as for imaging ellipsometry. Polarizer angles were determined with a precision of 0.01 and the intensity was measured with a lock-in amplifier (Princeton Applied Research, Princeton, N.J.).

Ex Situ Ellipsometry. Before adsorption of thioredoxin-ELP fusion protein, the thickness of HDT and MUOH SAMs on gold were separately measured by ellipsometry. Then, the gold substrates presenting HDT and MUOH SAMs were immersed into 2 ml of PBS solution containing 1 $\mu$M thioredoxin-ELP, and NaCl was dissolved in the solution. After incubation for 10 min, the substrate was rinsed with water several times and dried in a stream of nitrogen. The thickness of HDT and MUOH SAMs on gold were measured again to examine the reversibility of adsorption of thioredoxin-ELP on HDT and MUOH SAMs on gold. A similar experiment was performed with 1 $\mu$M Alexa 488 labeled as a control. Ellipsometric constants of the substrate were measured in air before and after modification with SAMs and adsorption of protein. The thicknesses of the films were calculated using a parallel slab model with assumed refractive indices of 1.0 for air and 1.5 for the SAMs and 1.45 for the thiroedoxin-ELP fusion protein.

In situ Ellipsometry. The SAMs were mounted on the ellipsometer stage in a cuvet and the cuvet was filled with 50 mM phosphate, pH 7.4, 1 M NaCl. The polarizer and analyzer angle of the thiol-functionalized gold substrate were measured in buffer and converted to ellipsometric parameters ($\psi$, $\Delta$). Next, a concentrated stock solution of thioredoxin/ELP fusion protein was pipetted into the cuvet to a final concentration of 1 $\mu$M. The time course of adsorption of the fusion protein on SAM-functionalized gold substrates was examined by in situ ellipsometry as the ELP underwent a hydrophilic-hydrophobic transition as NaCl was added to the cuvet. The polarizer and analyzer angles were monitored after each increment of NaCl and were used in a nonlinear regression simulation program to obtain thickness and complex refractive indices for the silicon substrate, silicon oxide, gold, SAM, and protein overlayers. Effective thickness of the protein adlayer was calculated assuming a protein refractive index of 1.45.

SPR Analysis. Typically, an HDT SAM on a gold-coated glass slide was mounted in an empty Biacore sensor cartridge using water-insoluble double-sided sticky tape. The sensor cartridge was docked into a BiacoreX SPR instrument, and a system check was performed to ensure the absence of leaks in the fluid path and minimal baseline drift. The cartridge was then removed from the instrument and cooled to low temperature (−20° C.). The sensor surface was incubated with 1 $\mu$M thioredoxin-ELP fusion protein in 2 M NaCl at ~4° C., warmed to room temperature to allow the fusion protein to undergo the phase transition, and adsorbed to the sensor surface for 5 min. Excess protein was washed away with buffered 2M NaCl at room temperature and the sensor cartridge was then reinserted into the BiacoreX instrument, which was maintained at 35° C. All buffers used for Biacore measurements were 50 mM potassium phosphate, pH 7.4 of varying NaCl concentrations.

Protein Patterning and Fluorescence Imaging. Unless otherwise noted, phosphate buffered saline (PBS) (0.01 M phosphate and 150 mM NaCl was adjusted to pH 7.4) was used as the low salt buffer. The gold substrate presenting patterned SAMs was immersed into 2 ml of a 1 $\mu$M solution of Alexa488 labeled thioredoxin-ELP in PBS at 4 C. Recrystallized NaCl was then added and dissolved in the solution to raise the salt concentration by 1.25 M,a nd the solution was warmed to room temperature. Under these solution conditions, the inverse transition occurs because $T_t$ (22 C)<$T_{solution}$ (~25 C). After incubation for 10 min, the substrate was rinsed in PBS at room temperature, 1.5 M NaCl and imaged in the same buffer on a BioRad MRC 1000 confocal microscope with a 10× or 20× objective. The confocal microscope was set at 10% power level and 1500 V detector gain. After imaging, the substrate was incubated in PBS for 5 min and extensively rinsed with PBS. The substrate was imaged in PBS under the same operating conditions of the confocal microscope to examine the reversibility of thioredoxin-ELP binding onto the patterned SAM on gold.

The antibody binding to the thioredoxin-ELP fusion protein was carried out as follows: first, unlabeled thioredoxin-ELP was adsorbed to the patterned SAM under solution conditions where T<$T_t$, as described previously. After rinsing the sample in PBS, 1.25 M NaCl, the sample was incubated with 0.5 $\mu$M FITC labeled anti-thioredoxin in PBS, 1.5 M NaCl for 30 min at room temperature. The substrate was imaged under a confocal microscope at 30% power level and 1500 V detector gain. After imaging, the substrate was incubated with PBS for 5 min and rinsed with PBS. The substrate was imaged again under the same operating conditions of the confocal microscope to examine the reversibility of the antibody pattern.

B. Results

Solution Characterization of Thioredoxin-ELP Fusion Protein. The inverse transition was spectrophotometrically characterized by monitoring solution turbidity as a function of temperature, due to aggregation of the ELP as it undergoes its inverse transition. The inverse transition of the thioredoxin-ELP fusion protein is shown in FIG. 13. As the temperature was raised, the turbidity of the solution, spectrophotometrically monitored by the optical density at 350 nm, remained constant up to a critical temperature. Further increase in temperature over a ~5° C. range resulted in an increase in turbidity to a maximum value. The change in turbidity with increasing temperature indicates the onset of the inverse phase transition due to the formation of aggregates of the thioredoxin-ELP fusion protein. The inverse transition temperature ($T_t$), defined as the temperature at the onset of the spectrophotometrically observed transition (5% of the maximum observed turbidity), is a convenient parameter to characterize the inverse transition. A thioredoxin control exhibited no change in absorbance with increasing temperature, indicating that the thermally induced aggregation observed for the thioredoxin-ELP fusion protein was due to the inverse transition of the ELP. The inverse phase transition is also completely reversible: the aggregates were resolubilized completely upon lowering the temperature below the $T_t$ and little hysterisis was observed in a thermal cycle (the up and down cycles are marked by arrows), as shown in FIG. 13.

The $T_t$ for a given ELP decreases with increasing ionic strength. By varying the ionic strength, the $T_t$ can therefore be modulated over a wide range (FIG. 13), which provides a convenient method to optimize the $T_t$ of a given ELP for a specific application (FIG. 13). Manipulating the solution temperature and ionic strength also provides experimental flexibility in inducing the inverse transition for a specific ELP. For example, in 150 mM NaCl, the $T_t$ is 43 C. The $T_t$ is greater than that of a solution, maintained at 4 C, and the thioredoxin-ELP fusion protein is therefore soluble. Upon increasing the NaCl concentration by 1.25 M and warming to room temperature, the $T_t$ decreases to ~22 C, which is the visible onset of the phase transition.

We sought to maximize pattern contrast—maximal, adsorption onto hydrophobic SAM with concomitant minimal adsorption on to the hydrophilic background SAM— and reversibilty of the patterns by ensuring that adsorption onto the patterned surface template occurred due to the phase transition rather than non-specific adsorption prior to the phase transition. We specified the following experimental parameters to achieve this objective: protein concentration, initial incubation time and temperature of the ELP fusion protein before induction of the ELP inverse transition, and the environmental trigger to drive the ELP phase transition. Because, protein adsorption onto surfaces is time, temperature and concentration dependent, we chose a dilute, 1 μM solution of the fusion protein to minimize nonspecific adsorption on the surface. Similarly, we exposed the patterned SAM to the thioredoxin-ELP fusion protein briefly (5 min) at 4° C., conditions chosen to minimize adsorption prior to the phase transition. Finally, we sought to drive the phase transition to the visible onset of turbidity to maximize interactions of the ELP with the surface rather than solution aggregation, as it underwent its hydrophilic-hydrophobic transition. This is because when the intramolecular transition is initiated, the polymer chains hydrophobically collapse, releasing waters of hydration to the bulk. This event is subsequently followed by intermolecular aggregation of the collapsed polymer chains, which is observed as an increase in solution turbidity. Because intermolecular aggregation is a secondary event, presumably with slower kinetics (which are dependent on polymer concentration) than the intramolecular transition itself, and because the solution is heated at typically 1° C. min$^{-1}$, the visible onset of turbidity at a NaCl concentration of 1.25 M indicates the occurrence of the phase transition.

Based on these considerations, we chose to induce the phase transition by adding 1.25 M NaCl to a 1 μM solution of thioredoxin-ELP in PBS at 4 C and warmed the solution to room temperature upto the visible onset of turbidity to pattern the thiroedoxin-ELP fusion protein onto the patterned SAMs. Under these conditions, the visible onset of turbidity occurs at ~22 C, slightly below room temperature. We also wished to minimize the salt required to induce the phase transition because of the effect of higher salt concentration on the interaction of thioredoxin with anti-thioredoxin, as discussed below.

Ellipsometry.

Ex Situ Measurements. A gold substrate was microcontact printed (μCP) with hexadecanethiol (HDT) using a flat polydimethylsiloxane (PDMS) stamp inked with 1 mM ethanol solution of the hydrophobic thiol. A part of the gold surface was brought in contact with the inked PDMS stamp so that HDT was transferred to only to half the surface, and formed a SAM in the region of contact. Next, the entire substrate was briefly incubated in a solution of MUOH which filled in the regions of the surface, which had not been in contact with the stamp, with the hydrophilic SAM. We measured the water contact angle and thickness of the surface by ellipsometry. The SAM formed from HDT by μCP was hydrophobic, with a water contact angle of 92, and its thickness measured byellipsometry was 1.8 nm (Table I). This surface is less hydrophobic than a control SAM of HDT created by self-assembly from a 1 mM solution of HDT in ethanol, which exhibited a sessile water contact angle of 105 . These results suggest that the HDT SAM prepared by μCP is probably less ordered than the HDT SAM prepared by solution self assembly. Alternatively, the SAM prepared by μCP using a flat stamp is less hydrophobic because it is subsequently incubated in a solution of MUD in ethanol, while the control, HDT SAM prepared by solution self assembly is not, which results in replacement of some fraction of HDT with MUOH, thereby lowering the water contact angle.

TABLE I

Thickness and contact angle measurements on hydrophobic and hydrophilic SAMs on gold.

| | Before ELP adsorption | | After ELP desorption |
|---|---|---|---|
| Sample | Thickness (nm) | Contact angle ($\Theta_a$ ($H_2O$)) | Thickness (nm) |
| Flat Stamp (HDT region) | 1.8 ± 0.1 | 92 ± 2° | 3.3 ± 0.2 |
| Flat Stamp (MUD region) | 1.4 ± 0.1 | 12 ± 2° | 1.9 ± 0.2 |
| Solution (HDT) | 1.7 ± 0.1 | 105 ± 1° | 3.2 ± 0.2 |
| Solution (MUD) | 1.4 ± 0.1 | 4 ± 2° | 1.8 ± 0.2 |

The thickness of the unstamped region of the surface, which was briefly incubated in MUOH, is 1.4 nm, and is similar to that of a control SAM of MUOH, prepared from solution. The water contact angle of 12 showed that the surface is hydrophilic, but is somewhat lower than the water contact angle of 4 of the control SAM prepared by solution self-assembly of MUD. The higher contact angle, we believe, is caused by the MUOH possible exposure of the methylene groups due to disorder in the SAM, because the brief incubation time does not allow the self assembly to proceed to equilibrium.

SPR Analysis of ELP Adsorption and Antibody Binding. The BiacoreX SPR instrument divides the sensor surface into two channels, which can be separately used to immobilize biomolecules. This allows one channel to be used as a reference, and all signals presented here are difference signals between channel 1 (measurement) and channel 2 (reference). As shown in FIG. 14, for the HDT SAM a signal difference between channel 1 and channel 2 of about 530 Response Units (RU) was observed [A], possibly due to small variations in substrate preparation. At time [1] the HDT SAM, to which the thioredoxin-ELP fusion protein was adsorbed above the $T_t$ outside the instrument was inserted [B] and a slight increase in signal difference of ~725 RU was observed, which was caused by the insertion process. The reference channel 2 was then rinsed with pure water for 5 minutes [2], which removed most of the adsorbed thioredoxin-ELP fusion protein from the sensor surface in this channel. The signal difference [C] of about 3300 RU corresponds to the amount of adsorbed thioredoxin-ELP fusion protein in channel 1.

At high salt concentration, 2 M NaCl in the running buffer, the signal was stable, but antibody binding was inefficient. Therefore the salt concentration in the running buffer was reduced to 1 M NaCl 131, which led to a slow desorption [D] of about 20% of the protein in about 1000 sec. The stable desorption rate was about 0.4 RU/sec. Next, channel 1 was selectively incubated with 50 μl anti-thioredoxin (1:10 dilution) in running buffer [4]. The signal increased by about 1600 RU [E] indicating significant antibody binding. Upon completion of binding, only the time-dependent desorption at a rate of 0.4 RU/sec was observed.

The sensor temperature can be changed in the BiacoreX, and although the temperature change is not linear with time, the temperature is measured at the sensor surface, and can be monitored as a function of time. Upon lowering the temperature [5] from 35° C. to 18° C. ($T_{solution}<T_t$) the signal [F] decreased to approximately the same level (400 RU) as the HDT SAM on gold.

The SPR measurements demonstrated that a thioredoxin-ELP fusion protein adsorbs to a hydrophobic surface and can be significantly desorbed by a small change of environmental conditions. The observation that after adsorption of the fusion protein, thioredoxin binds to an anti-thioredoxin mAb, suggests that the thioredoxin is exposed to the bulk and accessible to binding by anti-thioredoxin. The immobilized complex is stable at the surface, because in a separate experiment after mAb binding, the SPR signal was stable in a buffer containing 2 M NaCl,t o within 0.08 RU/sec over several hours, though the affinity for initial antibody binding is reduced at these salt concentrations (data not shown). Together, these independent experiments show that the noncovalent complex of fusion protein and antibody can be immobilized on the surface with high stability. Finally, the complex can be desorbed to a significant extent from the surface by lowering the temperature below the phase transition temperature. These results show that binding and desorption of the ELP-antibody complex is significantly reversible, but do not allow us to claim that complete and absolute reversibilty in desorption because the SPR measurements are relative to a reference channel that may not show complete desorption of the fusion protein upon rinsing in water.

Figure 15:
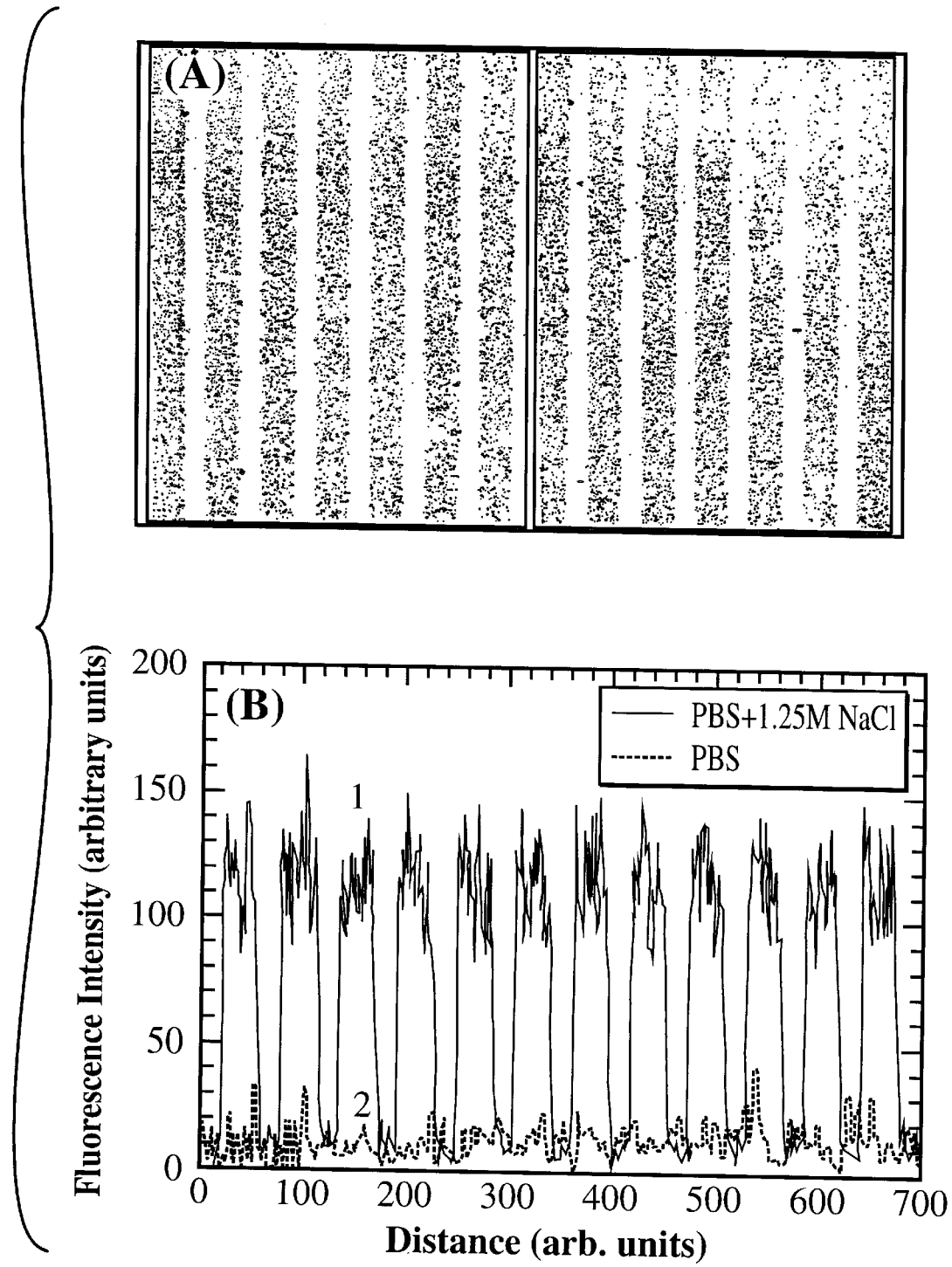

Dynamic Patterning of Thioredoxin-ELP Fusion Proteins. We fabricated a pattern of alternating 40 μm wide lines of HDT against a background of a MUOH SAM on gold by μCP. The patterned SAM was then incubated in Alexa488-labeled thioredoxin-ELP fusion protein (1 μM) in low ionic strength buffer for 5 min. at 4 C ($T<T_t$). Recrystallized NaCl was added to a final concentration of 1.25 M and the SAM was incubated for a further 5 min at room temperature. The SAM was then removed from the solution, washed in the high ionic strength buffer not containing any protein (PBS, 1.5 M NaCl, pH 7.4) and then imaged under a fluorescence microscope. The fluorescence image shown in FIG. 15 shows significant contrast between the alternating hydrophobic and hydrophilic stripes, indicating the preferential adsorption of the thioredoxin-ELP fusion protein to the patterned hydrophobic SAM. This result indicates that as the ELP becomes more hydrophobic upon undergoing its inverse transition isothermally due to the addition of NaCl, the fusion protein is preferentially driven to, and adsorbs to the patterned hydrophobic regions on the surface, mediated by hydrophobic interactions between the hydrophobic ELP and the methyl-terminated SAM. A line profile of the fluorescence intensity in FIG. 15B shows that high pattern contrast can be obtained by TRAP. The SAM was then incubated in a low ionic strength buffer (PBS) at 4 C, conditions that induce reversal of the ELP phase transition. Upon washing the surface with a low salt buffer ($T<T_t$), the fluorescence contrast in the sample vanished (FIG. 15B, line profile 2), indicating reversibility of protein patterning because of resolvation of the ELP, and consequently decreased hydrophobic interaction between the ELP and the HDT SAM.

The SPR results showed that that the preferential binding of the ELP to the hydrophobic SAM above the $T_t$ oriented thioredoxin such that is accessible for binding from solution. A HDT/MUOH SAM was patterned as before, and then incubated in 1 μM thioredoxin-ELP under low ionic strength at 4 C so that $T<T_t$. Next, the ionic strength of NaCl was increased by 1.25 M, and th solution warmed to room temperature to induce the phase transition and thereby pattern the fusion protein onto the surface by hydrophobic interactions. The SAM was then removed and washed in a high ionic strength to remove loosely adsorbed protein. The SAM was incubated in FITC-labeled monoclonal anti-thioredoxin antibody (0.1 μM) for 15 min. The SAM was then washed in high ionic strength buffer and imaged by fluorescence microscopy (FIG. 16A). The fluorescence image, especially the line profile in FIG. 5B clearly shows the preferential binding of the anti-thioredoxin to the thioredoxin-ELP adsorbed on the HDT SAM. In contrast, little antibody binding is observed on the regions that were patterned with MUD. Because the antibody is sensitive to submonolayer coverage of thioredoxin, the observed contrast confirms the successful patterning of the thioredoxin-ELP fusion protein on the patterned SAMs. Furthermore, these results also demonstrate that that the patterned thioredoxin is accessible to its ligand, a thioredoxin antibody from solution.

After imaging the bound complex on the surface by fluorescence microscopy, the sample was removed form the high salt buffer, and thoroughly washed in PBS at 4° C., solution conditions that reverse the transition. After washing, the sample was imaged, and the line profile of fluorescence intensity clearly shows that most of the bound complex desorbed from the surface due to the reversibility of the inverse transition. Upon reducing the temperature and ionic strength, the ELP resolvates and becomes hydrophilic. Solvation of the ELP diminishes the hydrophobic interaction between the ELP and the hydrophobic surface, which, we postulate drives desorption of the bound complex from the surface.

In Situ Ellipsometry. Although ex situ ellipsometry in air is experimentally simpler and therefore more convenient, it does not enable the final thickness of the adlayer to be measured because drying the films leads to a large, extraneous contribution to the film thickness due to crystallization of salt. We therefore carried out in situ measurements of adsorption and desorption using in situ ellipsometry. We examined the effect of increasing the salt concentration to isothermally induce the ELP phase transition at room temperature by in situ ellipsometry of unlabeled thioredoxin-ELP fusion protein on monolayers of a HDT (hydrophobic) and MUOH (hydrophilic) SAM on gold.

In separate experiments, the SAMs were mounted on the ellipsometer in a cuvet containing PBS, 150 mM NaCl., pH 7.4, and concentrated 4 M NaCl was added in step wise increments to raise the NaCl concentration (data not shown). The in situ ellipsometry revealed that the final steady sate thickness of the protein was ~120 Å on the HDT SAM and ~100 Å on the MUOH at 1.8 M NaCl, conditions under which $T_{solution}$ is well above the $T_t$ of the ELP. The extent of adsorption on the MUOH SAM is greater than that suggested by the patterning experiments conducted using fluorescence measurments. There are a number of experimental differences between the two experiments, such as initial adsorption temperature and time (4 C, 5 min for patterning, versus room temperature for in situ ellipsometry), and a higher final salt concentration for the in situ ellipsometry measurements; putuative causes of the different results obtained by in situ ellipsometry and fluorescence microscopy are summarized in the Discussion section of this paper.

Decreasing the salt concentration, by replacing the buffer with lower salt cocnentration, resulted in partial desorption of the fusion protein. The samples were then removed from the cuvet and washed extensively in water. The samples were dried, and the thickness were measured again in air, and showed a further decrease in the thickness of the both adlayers. These results show partial, 80% reversibility of adsorption of the thioredoxin-ELP fusion on both SAMs after extensive rinsing in water, and are qualitatively consistent with the fluorescence measurements.

C. Discussion

Because protein adsorption mediated by hydrophobic interactions on patterned hydrophobic SAMs (against a protein resistant background) is perhaps the most generic protein patterning method, we have focused on modulating the hydrophobic interaction between a protein and a hydrophobic surface to allow reversible binding of proteins to surfaces. We hypothesized that because hydrophobic interactions are entropically driven by the desolvation of a hydrophobic interface, triggered solvation and desolvation of the interface would enable control of the hydrophobic protein-surface interaction. In principle, this can be achieved by two complementary methods: (1) creating a surface whose surface energy can be switched by an external, environmental trigger, and (2) a protein whose solvation can be externally modulated. We have chosen to initially demonstrate this principle using the latter route, namely by controlling the interaction between an elastin fusion protein, where the elastin tail can be reversibly switched between two states—a hydrophilic solvated state below its inverse transition temperature, and a hydrophobic, desolvated state above its inverse transition temperature.

We therefore sought to create dynamic protein patterns by modulating the adsorption of proteins, by environmental, solution control of the hydrophobic interaction between a protein and surface. We achieved reversible, triggered solvation-desolvation of a model protein by synthesizing fusion proteins which incorporated a C-terminal polypeptide tag which exhibits thermally (or ionically) reversible salvation in response to alterations in the environmental conditions. The tag is an elastin-like polypeptide which undergoes a thermally reversible inverse phase transition in response to alterations in temperature or ionic strength.

We examined the interaction between the thioredoxin-ELP fusion protein and a patterned SAM containing a hydrophilic and hydrophobic region at the micrometer scale in response to the inverse transition. The preferential and reversible adsorption of ELP fusion proteins on hydrophobic substrates enables reversible protein patterning by thermodynamically directing an ELP fusion protein above its $T_t$ selectively onto micropatterned hydrophobic regions against a hydrophilic background. We call this method thermodynamically addressable reversible patterning (TRAP), and it is potentially applicable to any molecule that contains a moiety that is capable of undergoing a reversible hydrophobic-hydrophilic transition. Patterning by TRAP using the inverse transition takes advantage of a "thermodynamic address": a surface template which exhibits patterned domains with different surface energies, which can be easily achieved by microwriting and $\mu$CP of thiols on gold as well as by phase segregation of block copolymers and polymer blends. The selective adsorption of ELP fusion proteins above their $T_t$ on patterned hydrophobic regions against a hydrophilic background, is then exploited to thermodynamically direct the fusion protein to patterned hydrophobic domains.

We have further shown that the thioredoxin-ELP patterns created on the patterned SAMs on gold are oriented such that some fraction of the thioredoxin is able to bind an anti-thioredoxin monoclonal antibody from solution, and that binding selectively occurs on the hydrophobic regions that are patterned with the thioredoxin-ELP fusion protein. Because selective binding of the antibody is observed on the hydrophobic regions, this suggests that the concentration of adsorbed thioredoxin-ELP fusion is minimal on the hydrophilic, OH-terminated regions. Finally, reversing the phase transition, by lowering the salt concentration resulted in essentially complete desorption of the antibody-thioredoxin complex from the surface. This is an important observation, because it shows that the selective binding of the antibody to the hydrophobic surface is not caused by direct hydrophobic interactions between the antibody and surface, but is instead due to specific molecular recognition between the antibody and thioredoxin. Finally, desorption of the bound antibody-fusion protein complex clearly suggests that desorption is caused by reversibility of the ELP phase transition.

The initial results reported here on dynamic protein patterning by TRAP are promising, but there are a number of significant differences between the results obtained by fluorescence microscopy and in situ ellipsometry that require further clarification. In situ ellipsometry showed significant binding of the thioredoxin-ELP fusion protein onto the hydrophilic MUOH SAM in its desolvated, hydrophobic state. There are a number of reasons that could account for this discrepancy. First, because ellipsometry measures the thickness change of all molecules adsorbed at the surface, a small concentration of a surface-active contaminant that binds preferentially to the surface, and is detected in ellipsometry but not by fluorescence microscopy (presumably because it was not labeled with Alexa due to a lack of accessible amine groups) could account for the differences observed by the two techniques. We believe this possibility to be unlikely, because the thioredoxin-ELP fusion protein was exhaustively purified prior to use.

An alternative reason for the discrepancy between in situ ellipsometry and fluorescence microscopy may lie in subtle, but important differences in experimental protocols such as the initial temperature and incubation time, differences in the enviornmental trigger used to induce the pahse transition in the two experiments, and well as in the rinsing procedure after adsorption of the thioredoxin-ELP fusion protein above its transition temperature. It is possible that the thiroedoxin-ELP fusion protein is weakly adsorbed to the hydrophilic surface, and is removed in the patterning experiments, but is retained in the in situ ellipsometry dies to differences in the extent and vigor of rinsing in the two separate experiments. The effect of the conjugation of the flurorophore on surface adsorption, as well as distance dependent quenching effects in fluorescence measurements on gold also cannot be discounted. Studies are in progress to elucidate the origin of these differences, as well as to optimize this patterning methodology by systematic investigation of the effect of surface chemistry (especially the use of oligoethylene glycol SAMs to suppress ELP adsorption onto the background) and experimental conditions on patterning by TRAP.

TRAP is an attractive methodology to dynamically pattern proteins on the micrometer scale on patterned hydrophobic templates because it is a generic method that is applicable to most soluble proteins. First, this is because the introduction of environmentally triggered properties in a target protein simply involves gene-level N or-C-terminal fusion of the peptide codons into a cloned or synthetic gene, which is easily achieved by standard molecular biology manipulations. Second, fusion proteins containing this polypeptide tag are rendered environmentally responsive, and this appears to be a general phenomenon. Finally, the ELP tag can be chemically conjugated to molecules that are not genetically encodable, thereby creating an environmentally-responsive bioconjugate that can be reversibly adsorbed and desorbed by small changes in solution conditions.

Because proteins are patterned reversibly by TRAP, unlike current methods for protein patterning, many applications can be envisioned for dynamic, smart proteins that have tunable surface properties that can be created by TRAP. Temporal control of protein patterns is desirable for a number of applications. TRAP has immediate application in patterning biomaterials with proteins or other biomolecular ligands to modulate cellular interactions. For example, dynamic protein patterns, where one or more proteins are patterned reversibly, would introduce a greater level of sophistication in the design of biomaterial surfaces that than is currently possible. For example, multiple extracellular matrix (ECM) proteins (or peptide ligands derived from ECM proteins) with different desorption triggers could be patterned simultaneously, but desorbed at different times, thereby providing temporal control of protein density on a spatially-patterned surface, which could potentially mimic the dynamic nature of the extracellular matrix.

Similarly, dynamic protein patterning is also likely to be useful in the regeneration of multianalyte biosensors and in BioMEMS to control surface properties. Specifically, the ability to bind and desorb protein by an external signal is useful in the regeneration of biosensors that are integrated into microfabricated devices containing microfluidics. This would enable delivery of an analyte binding protein—the sensing molecule—to a chip surface under conditions that induce the inverse transition of the ELP tag and thereby promotes hydrophobic interaction between the protein and sensor surface via the ELP tag. After analyte binding and detection, in response to an environmental trigger—a modest change in solution conditions such as decrease in temperature or ionic strength—the ELP solvates, which enables the bound complex to be desorbed from the surface, thereby regenerating the surface back to initial conditions. Incorporation of a microfluidic system into the microfabricated biosensor would enable analyte binding protein to be delivered to the surface and bound by inducing the inverse transition for a subsequent round of analyte detection. These concepts can be further extended to reversibly pattern an array of different proteins onto preformed, patterned SAM templates to create proteomic arrays that are capable of releasing a bound complex to solution for downstream analysis.

The foregoing is illustrative of the present invention, and is not to be construed as limiting thereof. The invention is defined by the following claims, with equivalents of the claims to be included therein.

I claim:

1. An article having a regenerable patterned surface for binding compounds of interest from an aqueous solution, said article comprising:
   (a) a solid support having a plurality of separate and discrete hydrophobic surfaces formed thereon; and
   (b) a conjugate reversibly bonded to each of said separate and discrete hydrophobic surfaces, said conjugate comprising (i) a bioelastic compound and (ii) a binding compound, wherein said binding compound specifically binds a compound of interest, and wherein said bioelastic compound has a transition temperature below which said bioelastic compound is soluble in said solution, and above which said bioelastic compound is insoluble in said solution; so that said surfaces may be used to bind a compound of interest at a temperature above said transition temperature, and so that said conjugate can be removed from said hydrophobic surface for recycling of said article by lowering the temperature of said solid support below said transition temperature.

2. The article according to claim 1, wherein said separate and discrete hydrophobic surfaces are separated by a hydrophilic surface.

3. The article according to claim 1, wherein conjugates bound to different ones of said separate and discrete hydrophobic surfaces have different bioelastic compound, so that different conjugates may be removed from different hydrophobic surfaces with different release conditions.

4. The article according to claim 1, wherein conjugates bound to different ones of said separate and discrete hydrophobic surfaces have different binding compounds, so that different compounds of interest are selectively bound at different ones of said separate and discrete hydrophobic surfaces.

5. The article according to claim 1, wherein said binding compound is a protein or peptide.

6. The article according to claim 1, wherein said binding compound is an antibody.

7. The article according to claim 1, wherein said compound of interest is a protein or peptide.

8. The article according to claim 1, wherein said compound of interest is an antibody.

9. The article according to claim 1, wherein said conjugate is a fusion protein.

10. The article according to claim 1, wherein said solid support is a gold support.

11. The article according to claim 1, wherein said solid support comprises a polymer.

12. The article according to claim 1, wherein said solid support comprises a metal.

13. The article according to claim 1, wherein said solid support comprises a semiconductor.

14. A method of recycling a regenerable article that has a patterned surface to which has been bound at least one compound of interest, said method comprising:

(a) providing an article comprising a solid support having a plurality of separate and discrete hydrophobic surfaces formed thereon and a conjugate reversibly bonded to each of said separate and discrete hydrophobic surfaces, said conjugate comprising (i) a bioelastic compound and (ii) a binding compound, wherein said binding compound specifically binds a compound of interest, and wherein said bioelastic compound has a transition temperature below which said bioelastic compound is soluble in said solution, and above which said bioelastic compound is insoluble in said solution; and then (b) separating said conjugate from each of said separate and discrete hydrophobic surfaces by lowering the temperature of said article to below a transition temperature of the bioelastic compound; and (c) binding a second conjugate to each of said separate and discrete hydrophobic surfaces on said regenerated article, said second conjugate comprising a second bioelastic compound and a second binding compound, so that said article may be reused.

15. The method according to claim 14, wherein said first conjugates and said second conjugates are the same at each of said separate and discrete hydrophobic surfaces.

16. The method according to claim 14, wherein said separate and discrete hydrophobic surfaces are separated by a hydrophilic surface.

17. The method according to claim 14, wherein conjugates bound to different ones of said separate and discrete hydrophobic surfaces have different bioelastic compound, so that different conjugates may be removed from different hydrophobic surfaces with different release conditions.

18. The method according to claim 14, wherein conjugates bound to different ones of said separate and discrete hydrophobic surfaces have different binding compounds, so that different compounds of interest are selectively bound at different ones of said separate and discrete hydrophobic surfaces.

19. The method according to claim 14, wherein said binding compound is a protein or peptide.

20. The method according to claim 14, wherein said binding compound is an antibody.

21. The method according to claim 14, wherein said compound of interest is a protein or peptide.

22. The method according to claim 14, wherein said compound of interest is an antibody.

23. The method according to claim 14, wherein said conjugate is a fusion protein.

24. The method according to claim 14, wherein said solid support is a gold support.

25. The method according to claim 14, wherein said solid support comprises a polymer.

26. The method according to claim 14, wherein said solid support comprises a metal.

27. The method according to claim 14, wherein said solid support comprises a semiconductor.

* * * * *

UNITED STATES PATENT AND TRADEMARK OFFICE
CERTIFICATE OF CORRECTION

PATENT NO. : 6,582,926 B1  Page 1 of 1
APPLICATION NO. : 09/695483
DATED : June 24, 2003
INVENTOR(S) : Ashutosh Chilkoti It is certified that error appears in the above-identified patent and that said Letters Patent is hereby corrected as shown below:

In the Brief Description of the Drawings:

Column 6, line 12 should read:  $T_t$ onto a HDT SAM on gold. The relative SPR signal Signed and Sealed this Second Day of January, 2007

JON W. DUDAS
*Director of the United States Patent and Trademark Office*